(12) United States Patent
Krause et al.

(10) Patent No.: US 11,253,306 B2
(45) Date of Patent: Feb. 22, 2022

(54) TOOL FOR THE MANIPULATION OF FASTENING DEVICES

(71) Applicants: William R. Krause, Charlottesville, VA (US); Daniel W Christensen, Amherst, VA (US)

(72) Inventors: William R. Krause, Charlottesville, VA (US); Daniel W Christensen, Amherst, VA (US)

( * ) Notice: Subject to any disclaimer, the term of this patent is extended or adjusted under 35 U.S.C. 154(b) by 0 days.

(21) Appl. No.: 17/021,408

(22) Filed: Sep. 15, 2020

(65) Prior Publication Data

US 2021/0282827 A1 Sep. 16, 2021

Related U.S. Application Data

(63) Continuation of application No. 16/818,978, filed on Mar. 13, 2020.

(51) Int. Cl.
| | |
|---|---|
| *A61B 17/88* | (2006.01) |
| *B25B 15/02* | (2006.01) |
| *B25B 15/00* | (2006.01) |
| *F16B 35/00* | (2006.01) |
| *A61B 17/86* | (2006.01) |
| *B25B 27/18* | (2006.01) |
| *A61B 17/00* | (2006.01) |

(52) U.S. Cl.
CPC ...... *A61B 17/8883* (2013.01); *A61B 17/8625* (2013.01); *B25B 15/002* (2013.01); *B25B 15/02* (2013.01); *F16B 35/00* (2013.01); *A61B 2017/00867* (2013.01); *B25B 27/18* (2013.01)

(58) Field of Classification Search
CPC ............ A61B 17/8875; A61B 17/8877; A61B 17/8888
See application file for complete search history.

(56) References Cited

U.S. PATENT DOCUMENTS

| | | | | |
|---|---|---|---|---|
| 7,175,626 | B2 * | 2/2007 | Neff .................... | A61B 17/7225 606/86 A |
| 2006/0079898 | A1 * | 4/2006 | Ainsworth ......... | A61B 17/8888 623/17.12 |
| 2010/0082033 | A1 * | 4/2010 | Germain ............ | A61B 17/1604 606/79 |
| 2014/0207233 | A1 * | 7/2014 | Steiner ................. | A61F 2/0805 623/13.14 |
| 2016/0030100 | A1 * | 2/2016 | Divincenzo ........ | A61B 17/8875 606/104 |
| 2016/0038201 | A1 * | 2/2016 | Cummings ........ | A61B 17/8615 606/304 |
| 2020/0289183 | A1 * | 9/2020 | Krause ................ | A61B 17/863 |

* cited by examiner

*Primary Examiner* — Nicholas W Woodall
(74) *Attorney, Agent, or Firm* — Kimberly O Snead

(57) ABSTRACT

A tool for manipulating flexible and non-flexible fastening devices. The tool assembly has a flexible rod for insertion into the distal end of the fastening device. A handle assembly interacts with proximal end of the flexible rod and the proximal end of the fastening device to control of the fastening device by initiating rotation at the distal end of the fastening device.

22 Claims, 23 Drawing Sheets

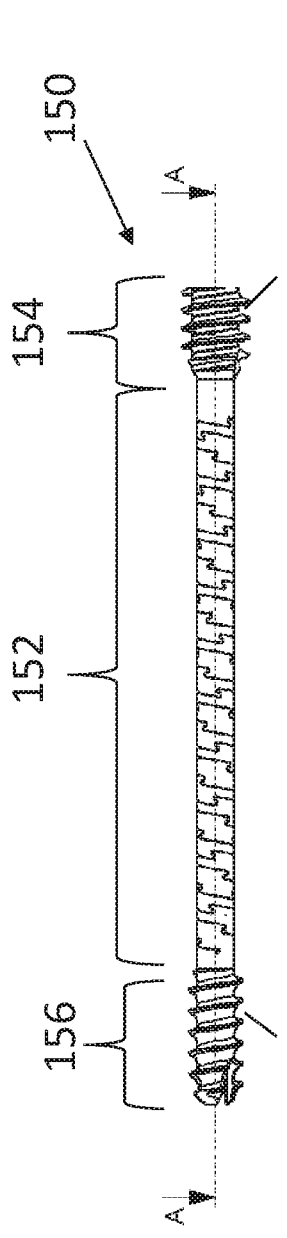
Figure 5
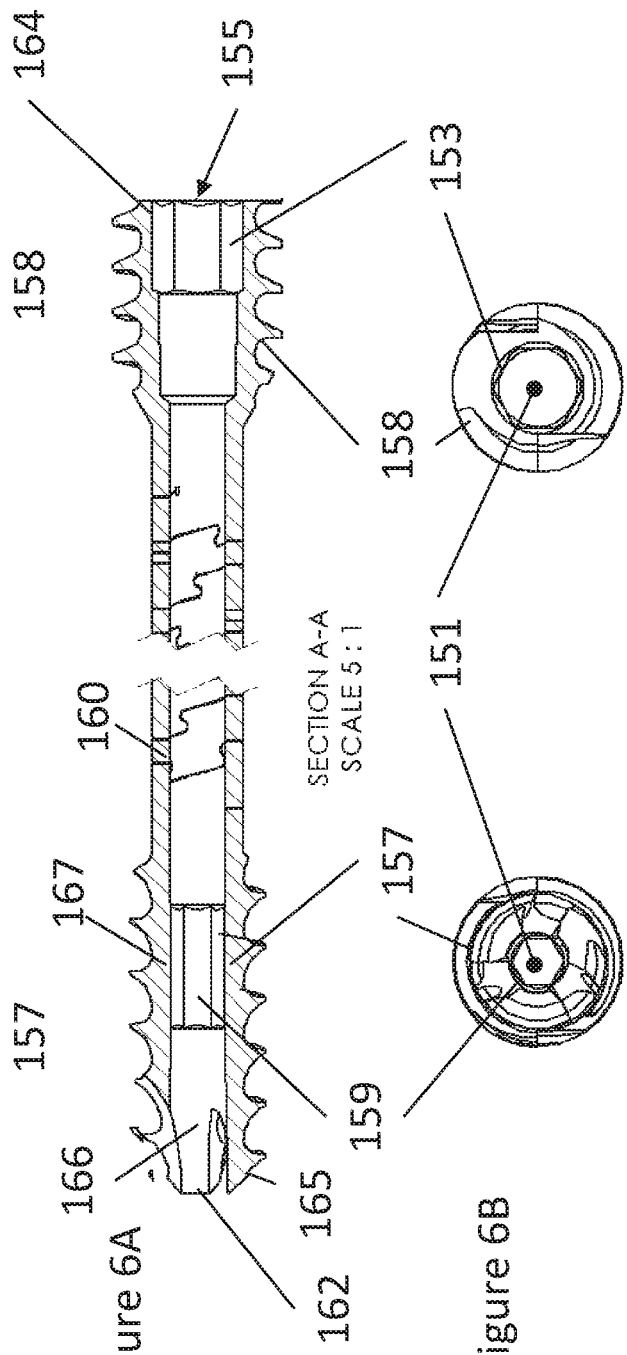
Figure 6A
Figure 6B
Figure 6C

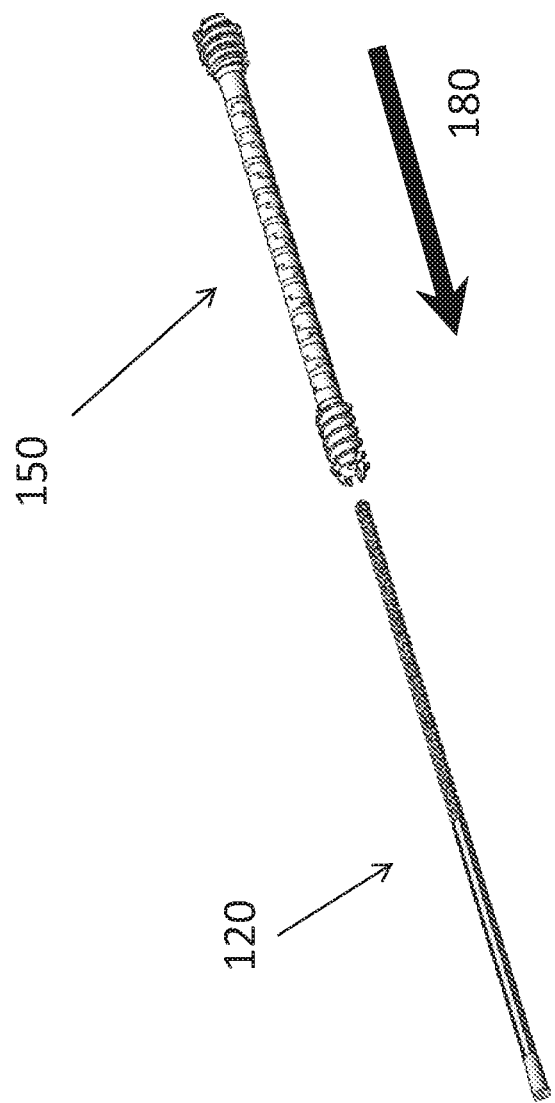

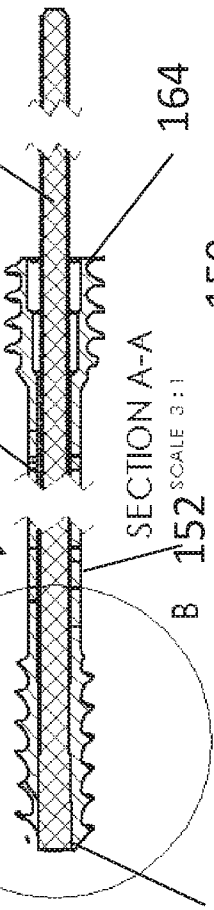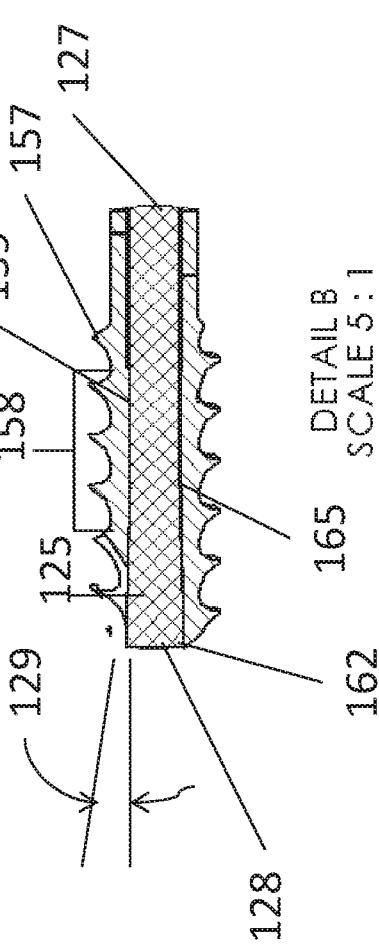
Figure 10A
Figure 10B
Figure 10C

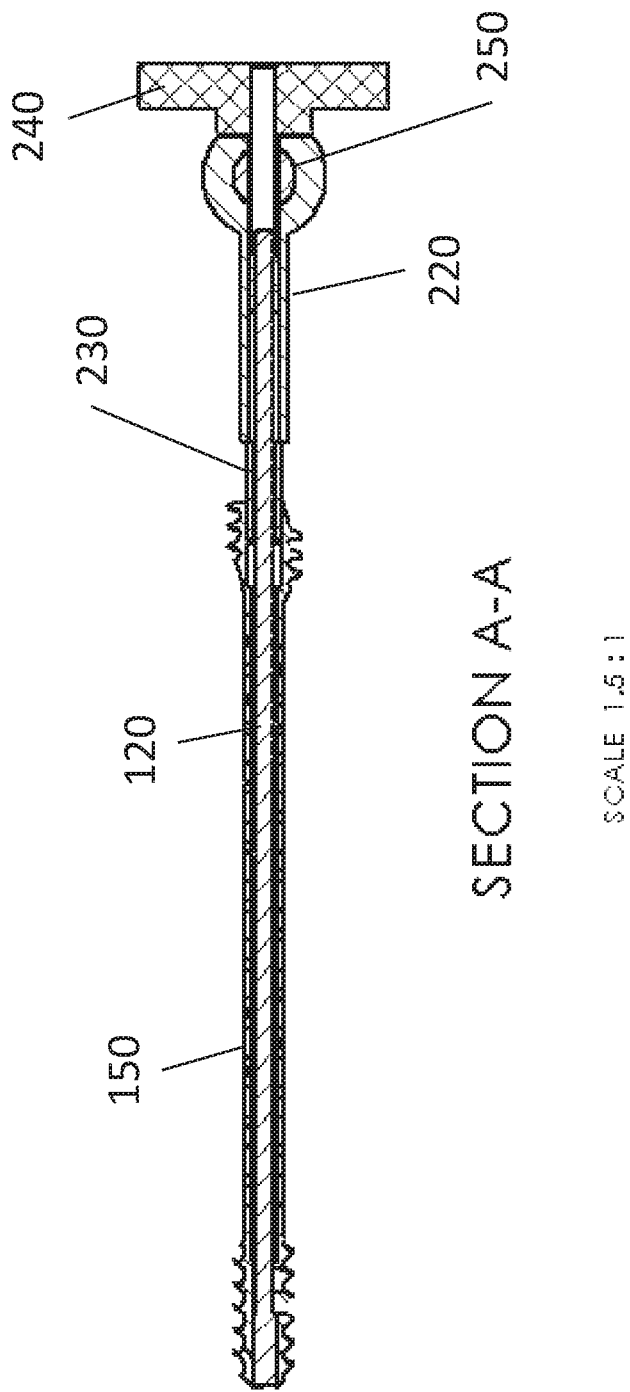

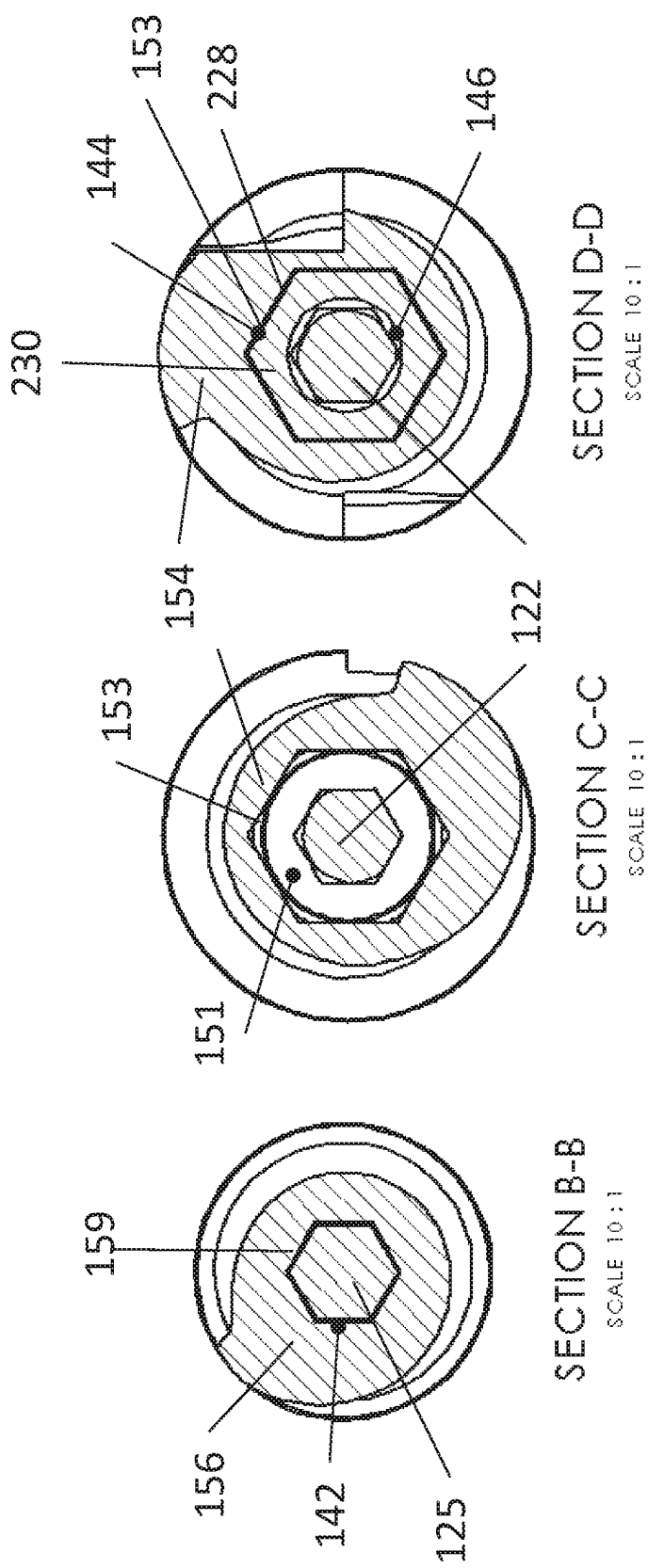

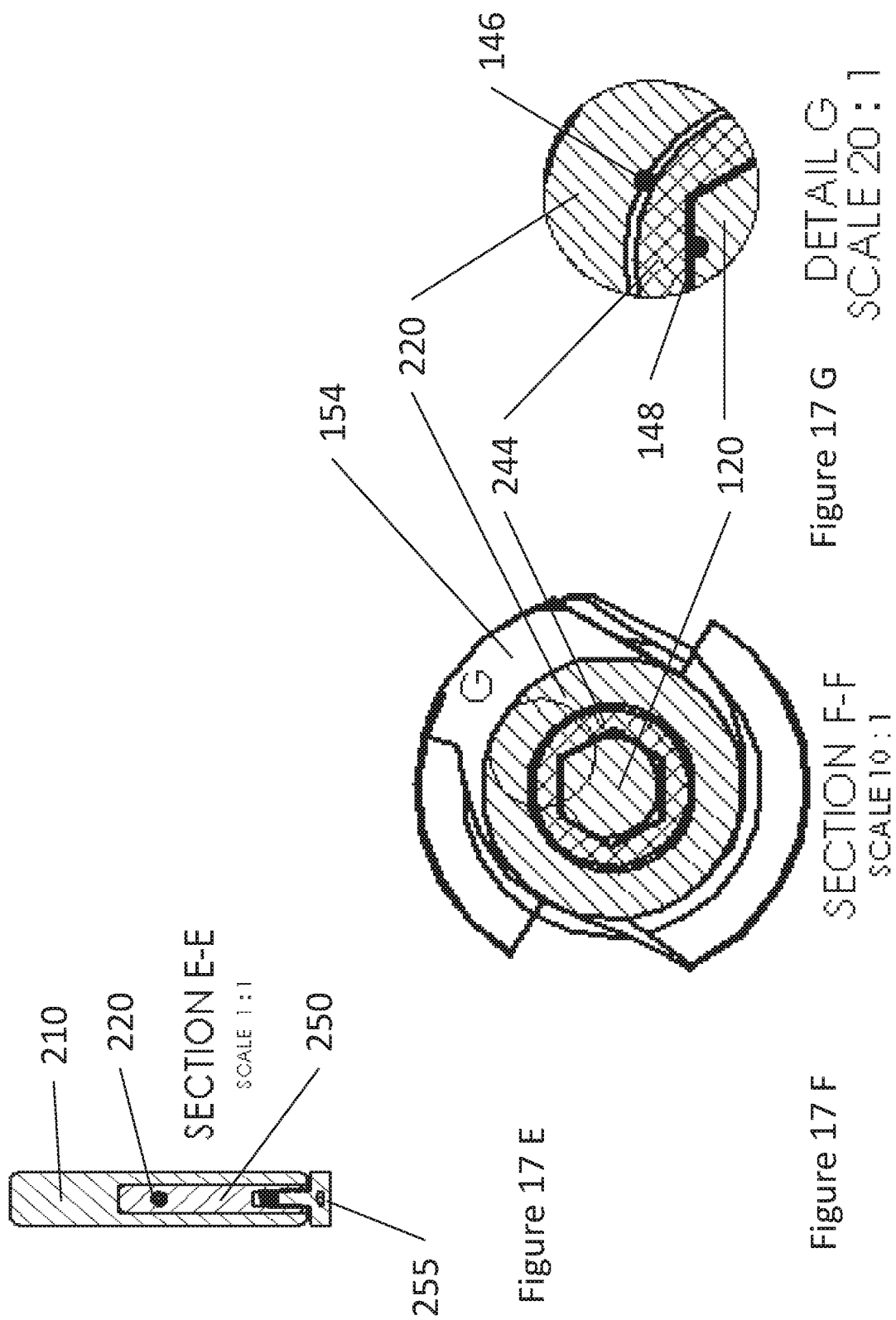

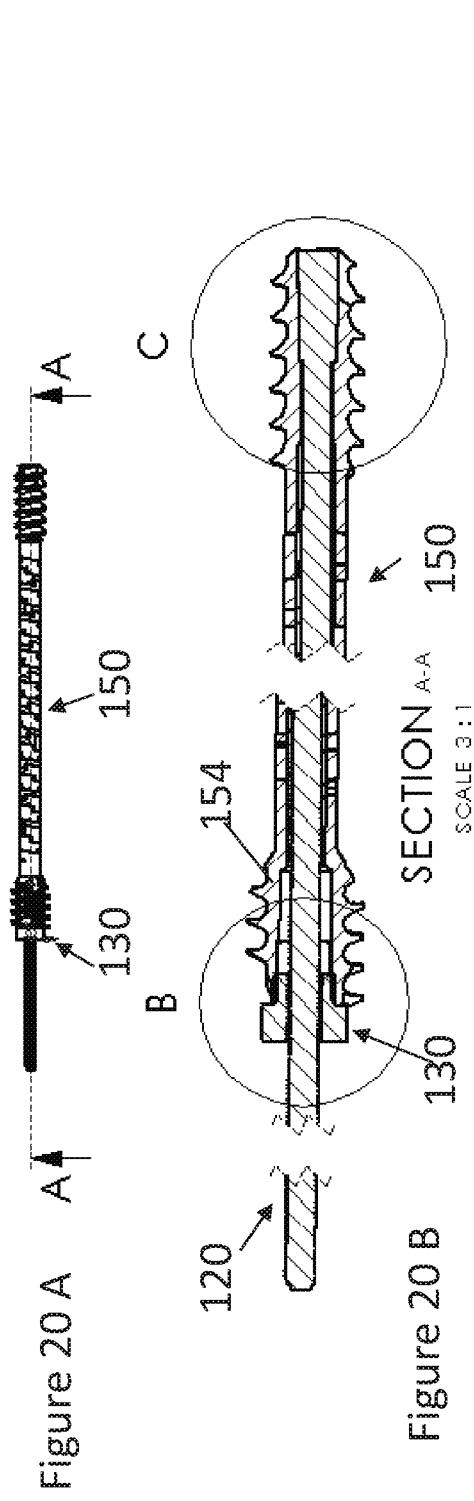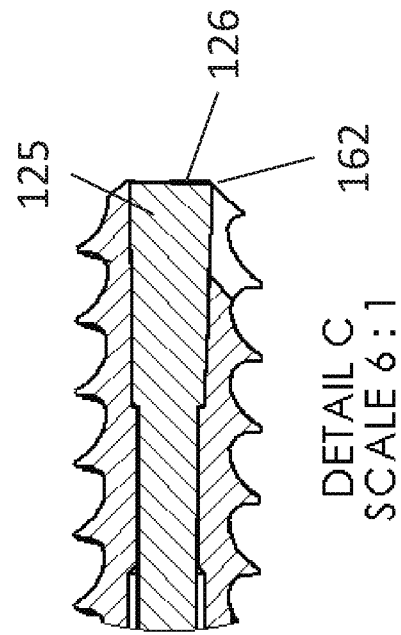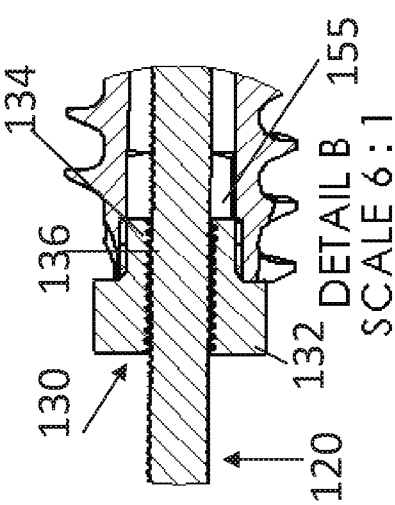

TOOL FOR THE MANIPULATION OF FASTENING DEVICES

FIELD OF THE INVENTION

The present invention pertains to a tool assembly for manipulating screws and, more particularly, to a tool assembly for manipulating flexible screws.

BACKGROUND

The application of flexible fastening devices encompasses a broad spectrum of industries, included, but not limited to, manufacturing, construction, mining, transportation, agriculture, aviation, automotive, and medical. Flexible fastening devices, either tipped like screws or flat end like bolts, have the characteristics of the cylindrical portion of the device being bendable about the longitudinal length. Flexible fastening devices are useable in many applications, from manufacturing to medical, to secure two objects together.

In manufacturing and construction, fastening devices are used to join curved members together, to join misaligned holes, to absorb vibration between two components and numerous other applications. In addition, flexible devices are used to connect two or more members whereby a straight passage of the bolt is impossible and a curved passage in one member allows the inserted flexible screw or bolt to follow the passage and be joined to another member. For example, two curved tubes can be connected by inserting a flexible bolt through the internal diameter of one to thread into the internal diameter of the other tube to join them together.

In the medical industry, flexible screws are particularly useful in the intramedullary fixation of fractured or severed bone fragments. Bone screws are typically used in internal fixation to anchor the fixation system to the relevant bone portions or to join two or more fragments of a fractured bone into close proximity for bone union. For example, screws can be used in plate or rod systems to treat complex fractures of long bones or conditions such as vertebral instability. In small bone fractures, such as the bones of the hands, feet and wrist, the screw is placed across the fracture site to bring the fracture surfaces in close proximity. In medium (clavicle, rib and others) and long (lower and upper extremities) bone fractures, screws can be inserted into the intramedullary canal for minimally invasive fracture reduction.

Various surgical procedures utilize devices to fixate anatomical tissue for healing. An example of a fixation device is a compression bone fixation screw, commonly referred to throughout the present description as "compression screw", used to fixate two or more bone fragments or intramedullary fixation of a bone.

A surgical screwdriver is commonly used to insert bone screws. This form of screwdriver has a drive shaft for rotating the screw and advancing it along the longitudinal axis of the driver. The driver cooperatively engages with a drive recess, within the proximal end of the screw, to help achieve axial alignment of the screw with the drive shaft of the screwdriver. The screwdriver also has means of preventing rotation of the screwdriver with the guide wire over which the screw is placed.

SUMMARY OF THE INVENTION

A tool assembly for manipulating a fastening device (150), such as a bone screw, of at least one element has a flexible guide rod (120), a fastening device (150), and a handle sub-assembly (200).

The flexible guide rod (120) is comprised of a proximal threaded section (121), a mid-section (123), and a distal section (125) having an outwardly tapered distal end. The outward taper is about 1 degree for a Morse taper fit and less than 90 degrees for a non-Morse taper fit. The flexible guide rod (120) has at least one cross-section configuration and a length greater than that of the fastening device (150) to extend through the proximal receptacle (155) of the fastening device (150) and engage with the guide rod mating passage (247) of the handle sub-assembly. The material for the flexible guide rod can be selected from the group consisting of Nitinol, spring steel, flexible polymers and flexible composites.

The fastening device has a distal segment (156) with an open tapered distal end (162); a proximal segment (154) with an open proximal end (164); and a central flexible segment (152) extending from the distal segment (156) to the proximal segment (154). The distal segment (156) and proximal segment (154) are preferably threaded.

The central flexible segment (152) has at least one sinuous slot running its length to provide flexibility and enable the connection of non-linear elements. A fastener channel (167), having at least one cross-section configuration, extends from the tapered distal end (162) of the distal segment (156) to the proximal receptacle (155) at the open proximal end 164. The cross-section configuration of the fastener channel (167) is complimentary to at least one of the cross-section configurations of the flexible guide rod (120). The tapered internal surface (166) of the distal end (156) of the fastening device (150) is tapered to the same degree as the distal tapered section (125) to enable the two elements to engage with one another. The tapered internal surface (166) of the fastening device (150) and the distal section (125) of the guide rod (120) are dimensioned to prevent the distal end (128) of the distal section (125) from passing through the distal end (162) of the fastening device (150). The cross-section of the distal alignment surface (159) of the fastening device (150) is complimentary to the predetermined configuration of the guide rod 120 to enable rotation.

A handle sub-assembly (200) has a handle (210) with a clamp orifice (212) extending into the handle (210) from a first end past a mid-point of the handle (210). A handle shank receiving area (211) extends through the handle (210) from the top to a handle shank (220) that extends from the bottom of the handle (210) from the bottom side of the handle (210). A coupling mechanism (230) extends from the handle shank (220) that is configured to receive proximal receptacle (155). A guide rod channel (228) that extends through the coupling mechanism (230) is configured to receive the proximal end of the flexible guide rod (120). The exterior of the coupling mechanism (230) has a cross section complementary to a cross section of a proximal mating surface (153) of the open proximal end (164) of the fastening device (150).

A guide rod shank passage (222) extends from the guide rod channel (228), through the handle shank (220) to the handle shank receiving area (211).

A guide rod holder clamp (250) having a securing member receiving area is dimensioned to be received within the clamp orifice (212), A guide rod hole (254) with the guide rod holder clamp (250) is dimensioned to align with the guide rod shank passage (222) and receive the flexible guide rod (120). A guide rod holder clamp securing member is configured to interact with the securing member receiving area. The securing member receiving area of the guide rod holder clamp (250) is optimally comprised of interior threads (252) and the tightening member a guide rod holder clamp screw (255) having threads (257) to interact with the interior threads (252).

A guide rod holder assembly (238) comprises a guide rod holder (240) and holder shaft (244). A holder shaft (244) has a guide rod mating passage (247) extending through a distal portion of the holder shaft (244); and a guide rod shaft passage (245) extending through a proximal portion of the holder shaft (244). The guide rod holder (240) and the guide rod shaft passage (245) are dimensioned to receive the flexible drive rod (120). The guide rod passage (245) is generally circular. The guide rod mating passage (247) has a cross-section complimentary to that of the guide rod (120) to enable rotation of the guide rod (120) by the guide rod holder (240).

One of the at least one cross-section configuration of the flexible guide rod is configured to interact with at least one of the at least one cross-section configuration of the fastener channel 167 to enable the fastening device to be inserted into or removed from at least one element. The guide rod (120) has a cross section less than an interior cross section of the distal segment (156) to create a gap (142) for torque transmission while enabling manipulation of the fastening device (150). The guide rod (120) cross section is less than the guide rod shaft passage (245) of the guide rod shaft (244) to create a gap (148) for torque transmission while enabling manipulation of the fastening device (150).

A locking nut, having interior threads (136) dimensioned to be received on the guide rod (120) proximal threaded section (121) and a body (130) dimensioned to be received within the proximal receptacle (155) of the fastening deice (150) is used to tighten pull the end of the screw toward the proximal end. This prevents movement by compressing the sinuous slot.

To use the tool assembly for the manipulation of a fastening device (150), a guide rod holder clamp (250), having a guide rod hole (254) and a threaded receiving area, is inserted into a clamp orifice (212) within the handle (210) of a handle sub-assembly (200). The guide rod hole (254) is aligned with a holder shaft receiving area (211) within the handle (210). A holder shaft (244) of a guide rod assembly (238) is extended through the holder shaft receiving area (211) and into a handle shank (220) that extends from a bottom side of the handle (210). The handle shank (220) has a coupling mechanism (230) at its proximal end configured to interact with the fastening device (150).

The proximal threaded section (121) of a flexible guide rod (120), having at least one cross-sectional configuration, is inserted into an open tapered distal end (162) of a fastening device (150). The fastening device (150) has a fastener channel (167) with a cross-sectional configuration. The flexible guide rod threaded section (121) is inserted through a distal segment (156) and a central flexible segment (152) to extend beyond a proximal segment (154) of the fastening device (150). The flexible guide rod (12) is further inserted through the fastener channel (167) until a tapered distal end (128) of a distal section (125) of guide rod (120) contacts the open tapered distal end (162) of the fastening device (150). The threaded section (121) of the flexible guide rod (120) is then inserted into a guide rod channel (228) within the coupling mechanism (230).

The coupling mechanism (230) is inserted then into a proximal receptacle (155) within a proximal segment (154) of fastening device (150) and the cross-section configuration of the proximal receptacle (155) and the cross section configuration of the coupling mechanism (230) aligned.

The cross-section configuration of the threaded section (121) is aligned with a cross section configuration of guide rod shaft passage (245) of holder shaft (244). Movement of the holder shaft (244) is prevented by pulling the guide rod hole (254) against the holder shaft (244) by inserting a threaded securing member into the guide rod holder clamp (250) receiving area.

The fastening device (150) is manipulated by rotating the guide rod holder (240) within the guide rod assembly (238) to engage the tapered distal section (125) of the guide rod (120) with the fastener channel (167) at the fastening device (150) distal segment (156). The fastening device (150) can be rotated or otherwise manipulated at both the distal end (128) and proximal receptacle (155), Once positioned the handle sub-assembly (200) is removed and a nut (130) threaded onto the threaded section (121). The tightening of the nut (130) pulls the tapered distal section (125) into tapered distal end (162) of fastening device (150). The excess threaded section (121) can then be removed.

BRIEF DESCRIPTION OF THE DRAWINGS

The objects, features, advantages and aspects of the present invention can be better understood with reference to the following detailed description of the preferred embodiments when read in conjunction with the appended drawing figures. All of the figures are drawn on an oversized scale, and like structure in different figures bears like reference numerals.

FIG. 4 A is a longitudinal view of the flexible guide rod 120 with a breakaway cut and showing locations of the detail views A and B and sectional views D and E;

FIG. 4 B shows the distal end 128 of the flexible guide rod 120 with an outward taper angle 129;

FIG. 4 C shows taper angle 129 of the distal end of the guide rod 120;

FIG. 4 D shows the fine threads 121 on the uniquely shaped guide rod threaded portion 122 at the proximal end of the guide rod 120;

FIG. 4 E shows the cross-sectional shape in the unthreaded mid-section 123 of the guide rod 120 at section C-C;

FIG. 4 F shows the cross-sectional shape of the proximal threaded section 122 of the guide rod 120 at section D-D;

FIG. 5 shows a fastening device 150 with its primary regions of the type applicable for medical use with the tool assembly of FIG. 1 in accordance with the disclosed invention;

FIG. 6A is a section view along plane A of the fastening device 150 of FIG. 5 in accordance with the invention;

FIG. 6B is a cross-sectional view of the threaded distal section 159 of FIG. 6A in accordance with the invention;

FIG. 6C is a cross-sectional view of the proximal section 158 of FIG. 6A in accordance with the invention;

FIG. 7 illustrates the fastening device 150 prior to sliding over guide rod 120;

FIG. 10A is a side view of the fastening device 150 fully engaged with the guide rod 120 and the location of Section A-A in accordance with the invention;

FIG. 10B is a cutaway view of Section A-A of FIG. 10A;

FIG. 10C is a detailed cutaway view of Section B of FIG. 10B;

FIG. 17A shows the longitudinal section A-A of FIG. 16;

FIG. 17B shows a cross sectional view B-B through the distal segment 156 of the fastening device 150 and the distal tapered end section 125 of guide rod 120 of FIG. 16;

FIG. 17C shows the cross-sectional view C-C through the distal portion of the proximal segment 154 of FIG. 16;

FIG. 17D shows the cross-sectional view C-C through the proximal portion of the proximal segment 154 of FIG. 16;

FIG. 17E is the sectional view E-E of the insertion tool handle 210 of FIG. 16;

FIG. 17F shows the cross-sectional view F-F through the insertion tool handle shank 220 of FIG. 16;

FIG. 17G is the detail area G-G shown in FIG. 17F;

FIG. 20A shows a lateral view of the locking nut 130 fully on the guide rod 120 and the location of Section A-A;

FIG. 20B shows the cross-section A-A and the location of detail areas B and C;

FIG. 20C shows the detail area B with the locking nut 130 fully engaged

FIG. 20D shows the detail area C with the taper end 128 fully engaged with the screw 150;

DETAILED DESCRIPTION OF THE INVENTION

Definitions

Figure 1:
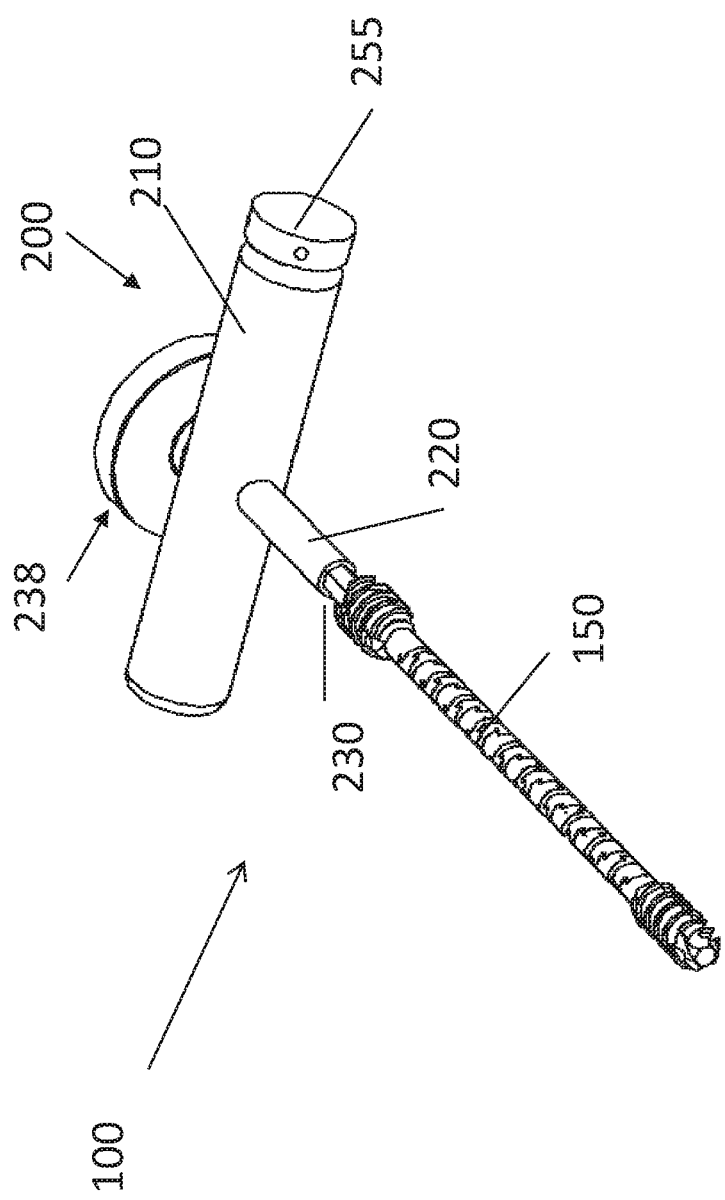
FIG. 1 is a perspective view of the tool assembly 100 with screw 150 and attached handle sub-assembly 200 in accordance with the disclosed invention.

As used herein the term "about" shall refer to plus or minus ten percent (10%).

As used herein the terms "fastening device", "screw", and "bolt" shall be used interchangeably and reference any flexible device that can secure two or more objects together.

As used herein the term "manipulation" or "manipulating" shall refer to inserting, removing, tightening, loosening, or adjusting of a screw; the terms "manipulation" or "manipulating" can be used interchangeably with "drive" or "driving" or "driven".

As used herein the term "compression fastening device" shall refer to any flexible device that can secure two or more objects together and tighten the contact through causing the fastening device to shorten.

As used herein the term "complimentary configuration" will mean shapes of interacting parts that interact with one another to prevent rotation of interacting parts individually.

As used herein the term "distal" shall refer to situation closer to the point of interaction between the tool assembly and an intended element.

As used herein the term "proximal" shall refer to situation farther away from the point of interaction between the tool assembly and an intended element.

As used herein the term "element" shall refer to any object or objects requiring the manipulation of a screw.

The use of flexible fasteners, such as bone screws, is hindered by the twisting of the screw when manipulated by the proximal end. In addition, broken screws within an element are also a problem and a mechanism or tool is needed to remove the distal portion of a broken screw.

It has been determined that in a screw having an interior cavity or channel, if the interior cavity of the distal end of a screw has a shape that is complimentary to the shape of a rod that can be inserted into the cavity from the proximal end, the screw can then be driven from the distal end. In this way, the screw can be inserted, removed, tightened, loosened, or otherwise adjusted as needed by application of force at the distal end of the screw. This is especially applicable when the screw is flexible and can be in a curved orientation, such as a bone cavity, through which the rod must pass to enter the distal end of the screw. The ideal choice of material for the guide rod portion of this application is Nitinol, a nickel-titanium alloy, although other metallic alloys or flexible polymers and composites meeting the criteria set forth herein are applicable.

Removal of a screw from the distal end also facilitates removal when the screw is broken. When inserted into the distal cavity, the complimentary rod can be used to rotate the screw in the opposite direction from insert, resulting in the screw backing itself out. Although it is common to back out a non-flexible screw, flexibility and screw length have prevented this from being easily accomplished heretofore.

Similarly, the rod can also be used to insert the screw. Thus, when coupled with a driving attachment to the proximal end of the screw, the driver would be applying the driving torque to both the distal and proximal ends of the screw thus relieving the twisting of the central flexible segment of the screw. For exemplary purposes, the insertion rod and internal complimentary shaped internal cavity are shown as hexagonal, but any complimentary shapes that do not allow rotation relative to one another are applicable.

Further, in prior art devices the alignment of the guide rod with the distal internal mating cavity and the mating cavity on the handle was dependent upon the alignment of the internal driving cavity at the distal end of the screw which receives the complimentary shaped driving coupling mechanism on the driver. This problem is eliminated in the disclosed system by having a separate element that is complimentary to the shape of the guide rod and is initially allowed to rotate freely but locks in place for driving the screw when necessary. In addition, other improvements have been incorporated into the design to ease manufacturing.

The disclosed driver couples at both the proximal and distal ends of the intended screw with following characteristics.

The embodiment illustrated in FIG. 1 shows the tool assembly 100 illustrating the handle sub-assembly 200 and attached fastening device 150 in accordance with the disclosed invention for the manipulation of screws such as insertion, removal, tightening, loosening, or other adjustment. The handle sub-assembly 200 enables the manipulation of both flexible, as well as inflexible, screws. The handle sub-assembly 200 comprises a handle 210, a handle shank 220, a coupling mechanism 230, guide rod holder clamp screw 255, and a guide rod holder assembly 238. The coupling mechanism 230 has an external configuration to interact with the proximal end of the intended fastening device 150. The flexible guide rod 120 penetrates the fastening device's 150 internal opening to couple with the device's internal distal end through complimentary tapered regions as described in more detail hereinafter.

Figure 2:
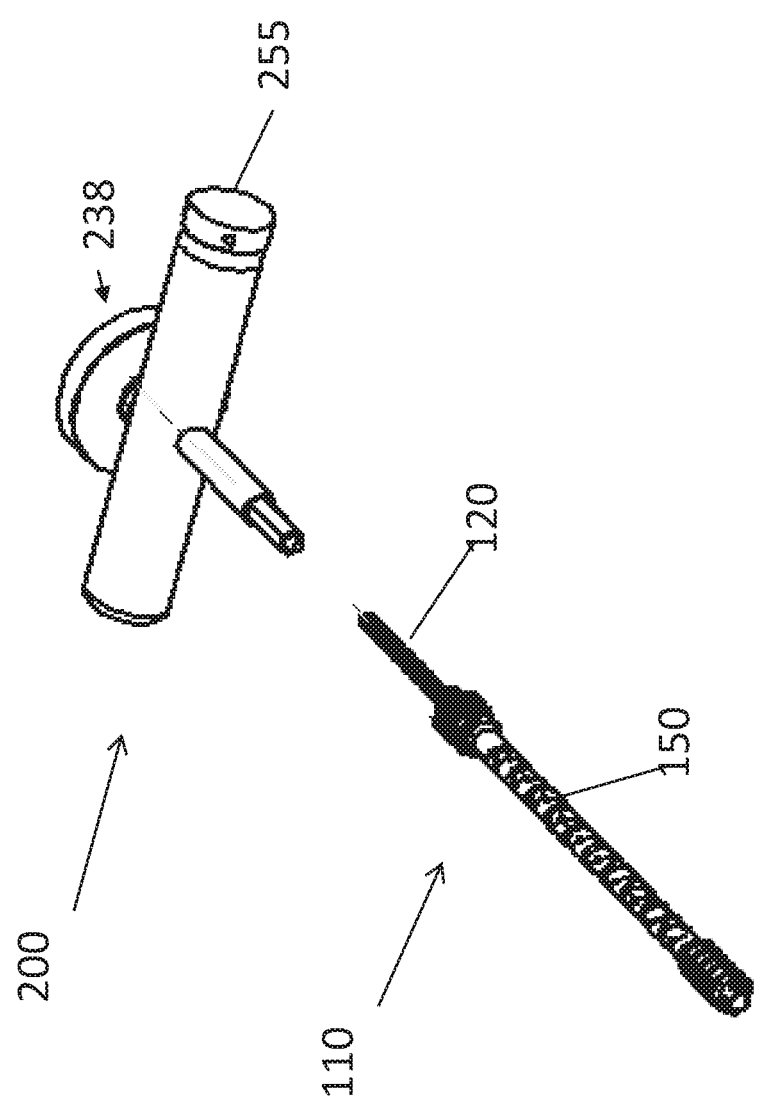
FIG. 2 is an isometric view of a screw 150 and guide rod sub-assembly 110 separated from the handle sub-assembly 200 in accordance with the invention.

As illustrated in FIG. 2, the guide rod sub-assembly 110 is composed of the guide rod 120 and fastening device 150 that are attached to the handle sub-assembly 200. When attached, guide rod 120 is secured within the handle sub-assembly 200 by the guide rod holder assembly 238 while fastening device 150 is secured to the handle sub-assembly 200 by coupling mechanism 230. The coupling mechanism 230 has an external configuration to interact with the proximal end of the intended fastening device 150.

Figure 3:
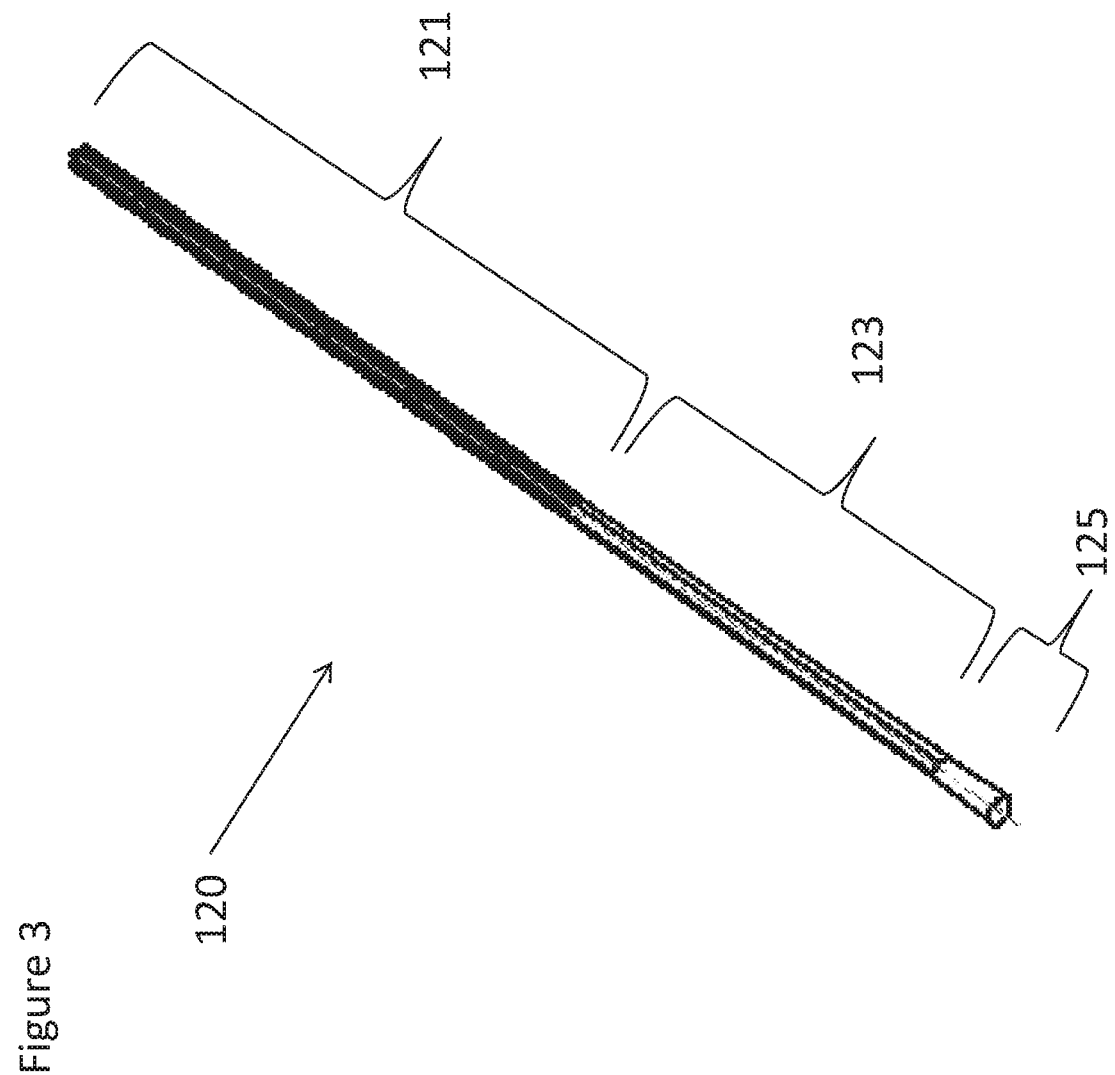
FIG. 3 illustrates a view of the flexible guide rod 120 of the guide rod sub-assembly of FIG. 2 in accordance with the invention.
Figure 4:
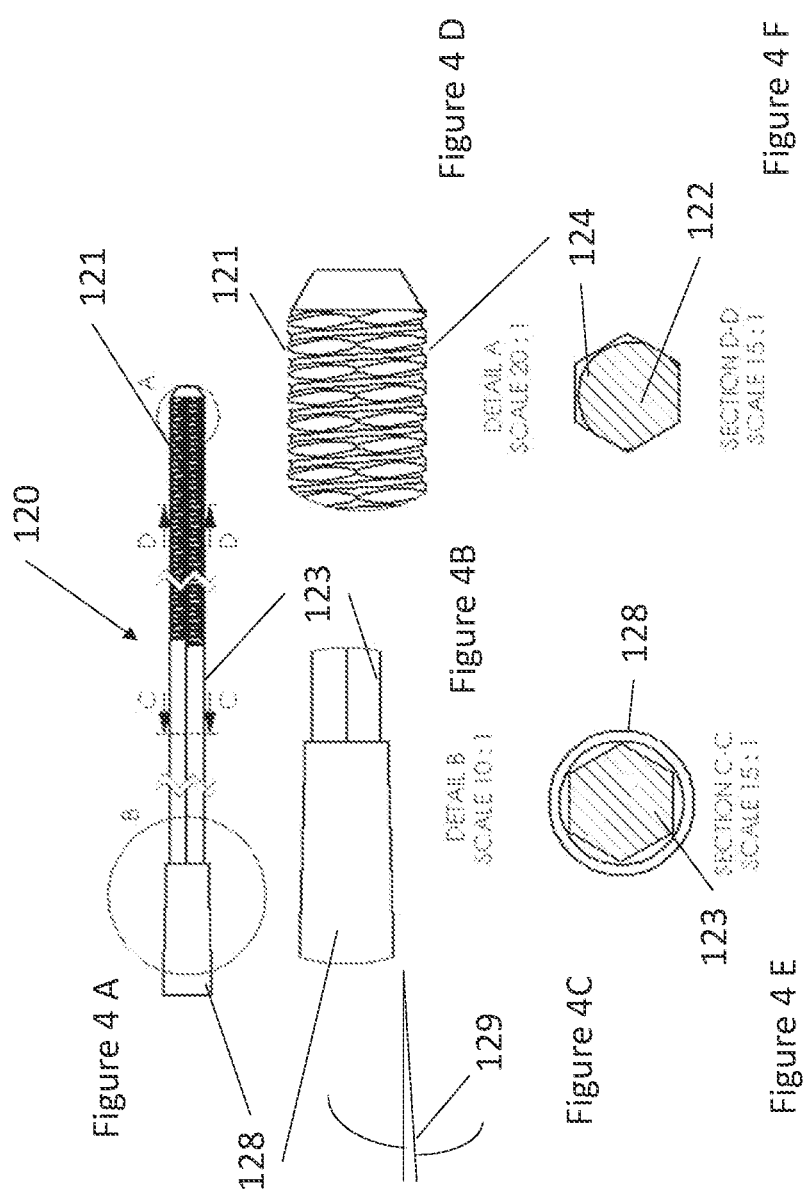
FIGS. 4 A-E illustrates a close and sectional views of flexible guide rod 120 in FIG. 3 in accordance with the invention.

Guide rod 120 is comprised of three sections as illustrated in FIGS. 3 and 4A F. The guide rod 120 typically has a unique cross-sectional shape that is complimentary to the distal alignment surface 159 of the fastening device 150. The guide rod 120 cross-sectional shape is shown as a hexagonal in FIGS. 4D and 4E. A hexagon is the preferred shape, but other shapes could provide the same functional results. The interior shape of the distal alignment surface 159 is complimentary to the guide rod's shape and sized to prevent excessive rotation between the two. As the tapered end 128 is not used to rotate the fastening device 150, the cross-sectional shape is preferably round for ease of manufacturing, however other shapes can be used. The rod 120 consists of the distal tapered end section 125, the mid-section 123, and the proximal threaded section 121. The flexible guide rod 120 penetrates the internal cavity of fastening device 150 wherein distal tapered section 125 couples with the internal distal end of fastening device 150 through complimentary tapered regions as described in more detail hereinafter. The proximal threaded section 121 is better illustrated in FIGS. 4A, 4C and 4E.

FIG. 4A provides a cross-sectional view of the guide rod 120 as well as identification of the areas illustrated in detail in subsequent figures, including the distal tapered end 128. FIG. 4D is a more detailed view of the fine threads 122 of the guide rod proximal threaded portion 121 of the guide rod 120. As shown in FIG. 4B, the distal tapered end section 125 has an outward taper towards the distal tapered end 128 with a taper angle 129 from about 1 degree for a Morse taper fit, to less than about 90 degrees for a non-Morse taper fit.

Figure 14:
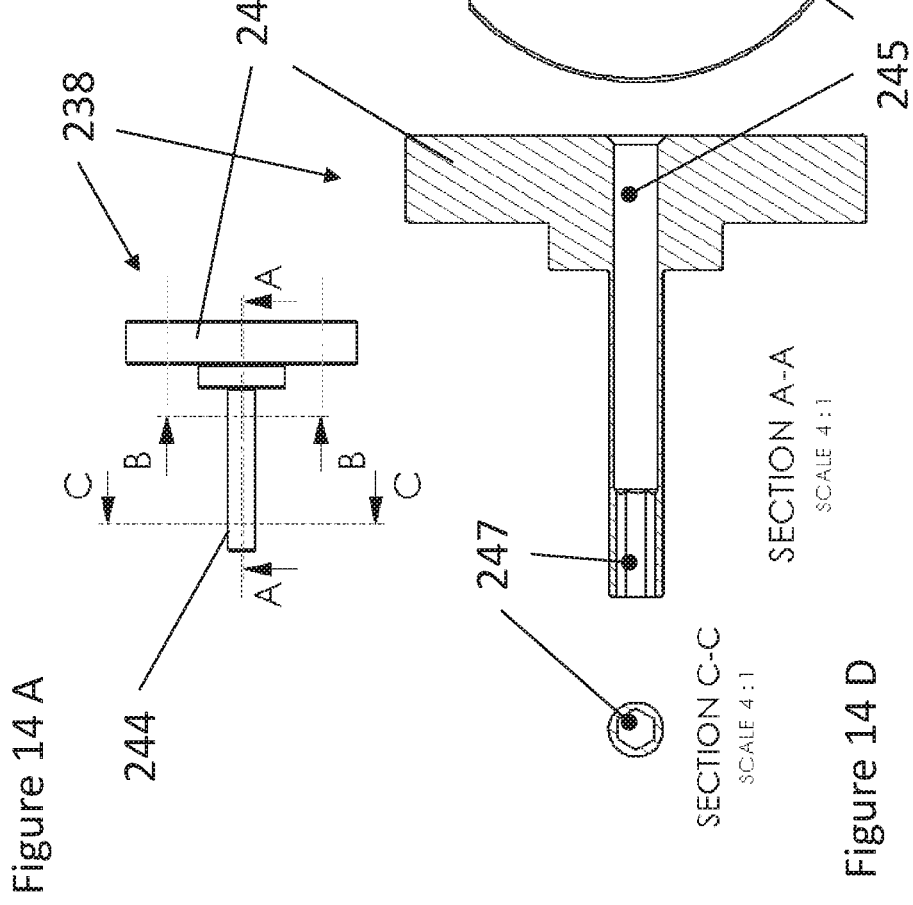
FIG. 14A is a side view of the guide rod assembly 238 showing the guide rod holder 240, holder shaft 244, and location of Section A-A.
FIG. 14B is the sectional view A-A of the guide rod holder 240.
FIG. 14C is a sectional view of B-B of FIG. 14A.
FIG. 14D is a sectional view of C-C of FIG. 14A.

The mid-section 123 has a unique cross-sectional shape, as shown in FIG. 4E, that is complimentary to the internal cavities of the fastening device 150 and the guide rod sub-assembly 238. For convenience, the guide rod 120 has a hexagonal shape as shown in the illustrations but could be one of numerous shapes that will prevent rotation between the fastening device 150 and the guide rod 120 and the guide rod holder 240 of the guide rod sub-assembly 238. FIG. 4F illustrates the section D-D through the threaded portion 121 of guide rod 120 showing the cross section of the rod 122 with the external threads 124. Due to the small diameter of the guide rod 120, about 1 to 5 mm, the guide rod holder 240 will have a small unique shaped interior cavity 245 (FIG. 14B).

FIG. 5 illustrates the fastening device 150 with its proximal segment 154 containing proximal threads 158, distal segment 156 with distal threads 157, and central flexible segment 152 therebetween. The cross-sectional view of FIG. 6A illustrates the proximal receptacle 155 for receiving the fastener coupling mechanism 230 of the handle sub-assembly 200 that is illustrated in detail in FIG. 11. For the sake of clarity and convenience, the proximal mating surface 153 of the proximal receptacle 155 is depicted as a hexagonal shape to receive a hexagonally shaped fastener coupling mechanism 230 on the handle sub-assembly 200. Preferably the proximal receptacle 155 and fastener coupling mechanism 230 are of the appropriate shape and complimentary to ensure an adequate transmission of torque for the fastening device 150 insertion or withdrawal. As with the proximal receptacle 155 and fastener coupling mechanism 230 requiring complimentary configurations, the distal alignment surface 159 and the unthreaded portion 127 of the guide rod 120 require complimentary configurations.

FIG. 6A also illustrates clearly the tapered internal surface 166 of the distal tapered exterior surface 165 of the fastening device 150. The tapered internal surface 166 has a taper complimentary to that of the tapered end 128 of the guide rod 120, thereby dimensioning the tapered end 128 to fit within the tapered internal surface 166. As the taper is wider at the distal end 162 of the fastening device 150 as well as the tapered end 128 of the guide rod 128, the complimentary taper will prevent the dislodging of the guide rod 120 during application of the locking nut 130 as described in more detail in FIG. 19. Also illustrated in this figure are the proximal end 164 of the proximal segment 154 and the helical slots 160 within the central flexible segment 152 of the fastening device 150.

FIGS. 6B and 6C show the end views of the fastening device 150 and its unique distal alignment surface 159 within the proximal receptacle 155 As illustrated in FIG. 6B the distal alignment surface 159 of the distal segment 156 is such that it mirrors the cross-sectional shape of the mid-section 123 of the guide rod 120.

The interior shape of the proximal segment 153 mirrors the exterior shape of the fastener coupling mechanism 230 of the handle sub-assembly 200.

FIG. 7 show the fastening device 150 about to be slide over the guide rod 120 during the course of insertion as shown in the direction of the arrow 180.

Figure 8:
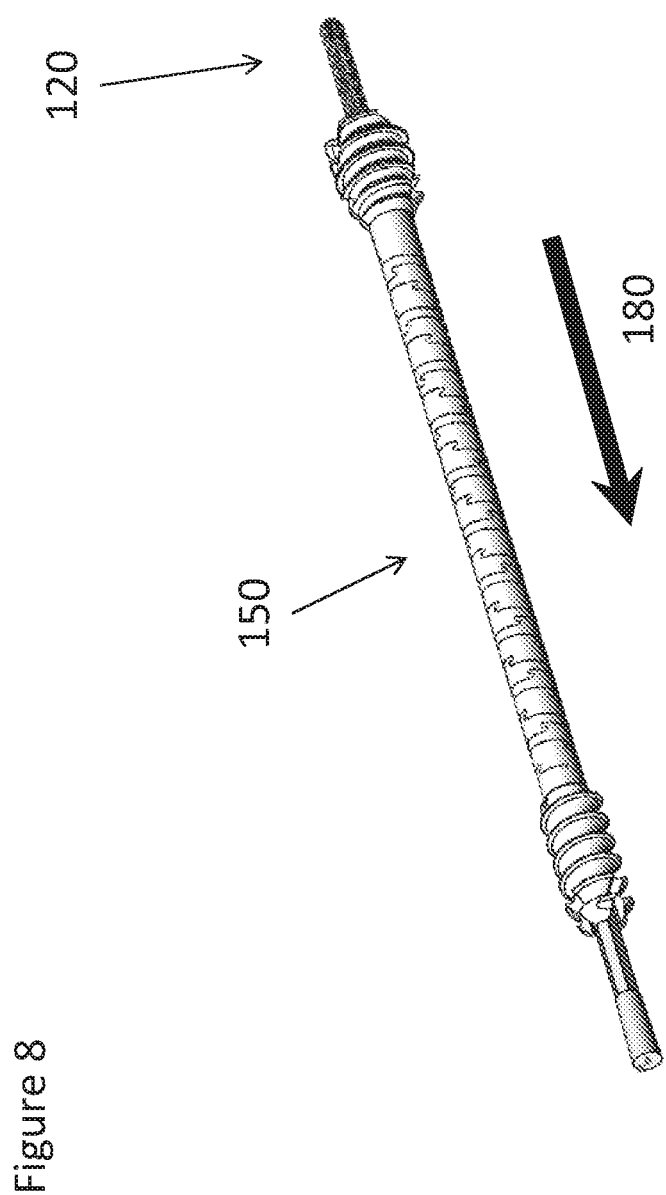
FIG. 8 illustrates the fastening device 150 sliding over guide rod 120.

FIG. 8 shows the fastening device 150 slid part way over the guide rod 120 during the course of insertion as shown in the direction of the arrow 180.

Figure 9:
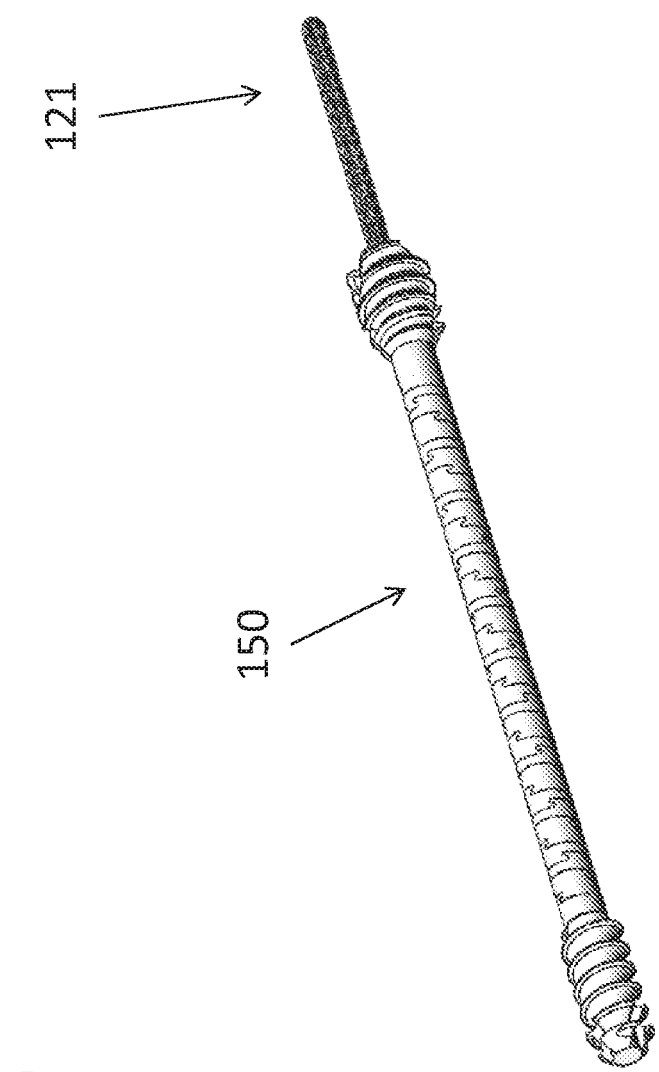
FIG. 9 illustrates the fastening device 150 fully engaged with the guide rod 120.

FIG. 9 shows the fastening device 150 slid all the way over the guide rod 120 during the course of insertion. The proximal threaded section 121 of the guide rod 120 extends beyond the fastening device 150 a sufficient distance to extend through the handle assembly 200 and into the guide rod assembly 238. The length of the guide rod 120 needs to pass into the guide rod assembly 238 a sufficient distance to be engaged for rotation. This facilitates manufacturing in that the guide rods 120 have the option be manufactured in approximate sizes, e.g. short, medium, and long rather than requiring exact sizing.

FIG. 10A shows the screw-guide rod assembly 110 and the location for Section A-A shown in FIG. 10B.

FIG. 10B shows Section view A-A with the location for Detail B. Shown is the fastening device 150 positioned over the guide rod 120. The guide rod 120 extends from the distal end 162 of the fastening device 150, though the central flexible segment 152 created by helical slots 160 and out through the open proximal end 164. The proximal threaded portion 122 of the guide rod 120 extends beyond the proximal end 164 of the fastening device 150 for passage and interaction with the insertion handle sub assembly 200.

FIG. 10C shows the Detail B of FIG. 10B and the distal tapered end section 125 and tapered end 128 of the guide rod 120 within the distal segment 156 of the fastening device 150. The taper angle 129 is such that the distal tapered end section 125 mates with the surface of the distal tapered surface 165 of the fastening device 150. The alignment between the tapered end 128 and the distal end 162 is also clearly shown in this figure. Typically, it is preferred that the taper angle 129 is that recommended for a Morse Taper in the order of 1 degree. During final installation, this will allow the distal tapered end section 125 of the guide rod 120 to be firmly joined to the distal tapered surface 165 of the fastening device 150 by means of a friction fit.

Figure 11:
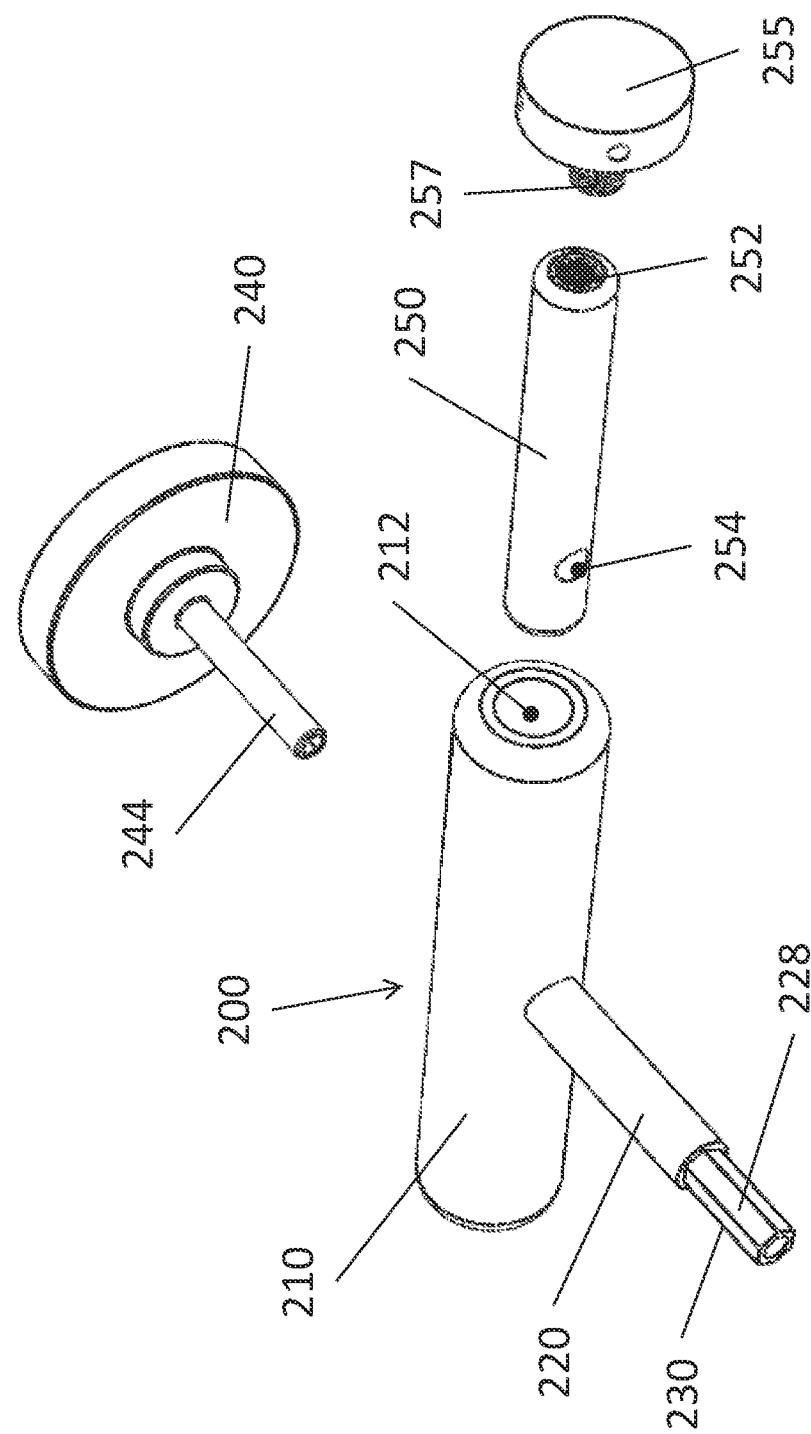
FIG. 11 shows an exploded view of the handle sub-assembly 200.
Figure 12:
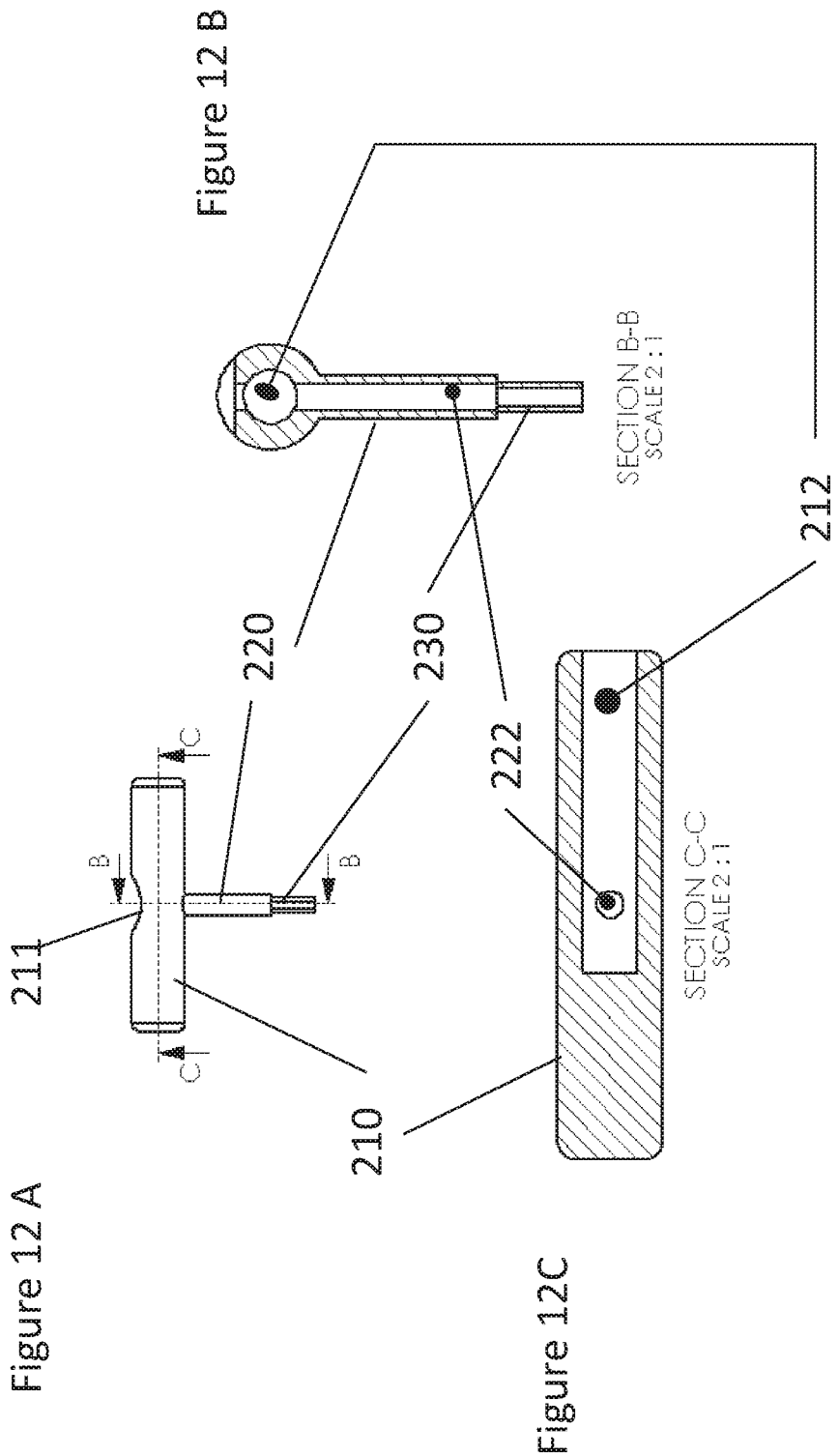
FIG. 12A shows the handle sub-assembly 200 for the location of the section lines B-B and C-C.
FIG. 12B is the detailed view of Section B-B in FIG. 12A.
FIG. 12C is the detailed view of Section C-C in FIG. 12A.

FIG. 11 illustrates an exploded view of the handle sub-assembly 200 and the component parts of the sub-assembly 200. The handle 210 has, at one end, a clamp orifice 212 that extends into the handle 210 past the guide rod shank passage 222 inside of handle shank 220 (FIG. 12B). The guide rod holder clamp 250 has a hole 254 which, when in place, aligns with the guide rod shank passage 222, illustrated more clearly in FIGS. 12 A-12C. The guide rod shank passage 222 is an extension of the guide rod channel 228 within the fastener coupling mechanism 230 and, in combination, they enable the guide rod 120 proximal threaded section 121 to interact with the complimentary interior of the guide rod mating passage 247 (FIG. 14A and FIG. 14D).

For use, the guide rod holder clamp 250 is inserted in clamp orifice 212 in the handle 210 such that the guide rod hole 254 is aligned with the guide rod shank passage 222 shown in FIG. 12B of the handle shank 220. This alignment is necessary so that the guide rod holder shaft 244 can be inserted into the guide rod shank passage 222. The clamp screw threads 257 of the guide rod holder clamp screw 255 are inserted into the internal threads 252 of the guide rod holder clamp 250. The guide rod holder clamp screw 255 is used to secure the guide rod holder 240 and handle shank 244 when it is inserted through the guide rod holder 240 within the insertion handle 210. Although the use of a guide rod holder clamp screw 255 engaging with the threads 252 within the guide rod holder clamp 250 is an easy to manufacture method of preventing movement of the guide rod 120, other methods as known in the art can be used.

It is critical during manufacture that the guide rod shank passage 222 and the guide rod hole 254 are aligned so that once the guide rod is inserted, the threading of the guide rod holder clamp screw 255 locks the holder shaft 244 in place.

FIG. 12 A illustrates the orientation of the sectional views in the front view of the handle sub-assembly 200 shown in FIGS. 12B and 12C for detail of the internal cavities of the part. The holder shaft 244 receiving area 211 is also illustrated in this figure. The holder shaft receiving area 211 is dimensioned to receive the holder shaft 244 in a manner to allow rotation and alignment without excessive side to side movement.

FIG. 12B shows the vertical section, Section B-B with the guide rod shank passage 222 running through the handle 210 and the length of the handle shank 220 and the channel within the fastener coupling mechanism 230 of the handle sub-assembly 200 for receiving the guide rod holder shaft 244 and the guide rod 120.

FIG. 12C shows the horizontal section, Section C-C of the handle 210 of FIG. 12A and the location and orientation of the guide rod shank passage 222 and clamp orifice 212 for the guide rod holder clamp 250.

Figure 13:
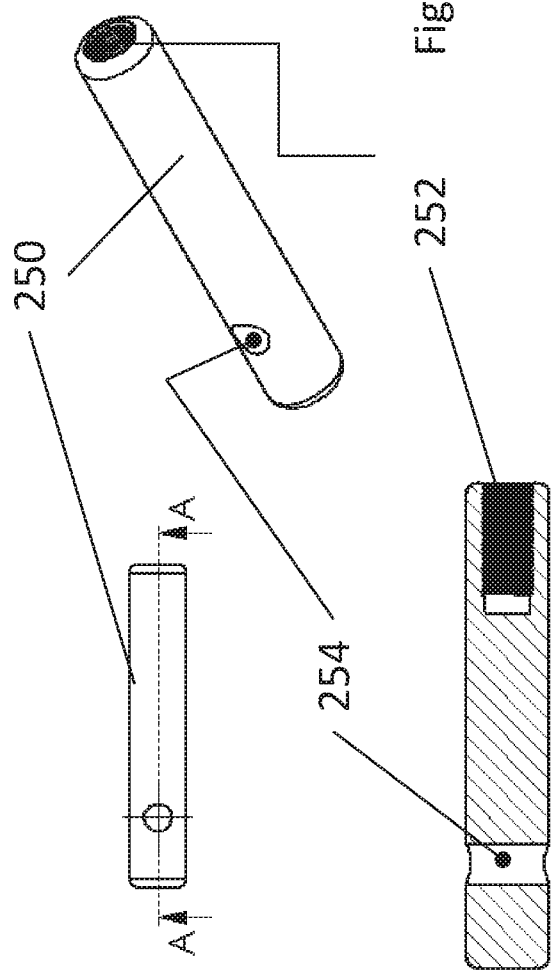
FIG. 13A is a top view of guide rod holder clamp 250 and location of Section A-A.
FIG. 13B is an isometric view of the guide rod holder clamp 250.
FIG. 13C is the sectional view A-A of the guide rod holder clamp 250.

FIGS. 13 A, 13B and 13C illustrate the top, isometric and longitudinal section view, respectively, of the guide rod holder clamp 250. The positioning of the internal threads 252 that engage the guide rod holder clamp screw 255 are clearly illustrated in this figure.

FIG. 14A illustrates the side view of the guide rod assembly 238, comprising the guide rod holder 240, holder shaft 244; and the locations of sectional views A-A, B-B and C-C. Longitudinal section A-A is shown in FIG. 14B illustrating the guide rod shaft passage 245 within holder shaft 244 for the passage of the guide rod 120 through the guide rod holder 240. The interior shape of the holder shaft 244 and thus the shape of guide rod shaft passage 245 is primarily circular as shown in FIG. 14C of Section B-B to provide unimpeded passage of the guide rod 120. However, the guide rod mating passage 247 of the distal end, or other section within the shaft, requires a shape complimentary to the cross sectional shape of the guide rod 120 as shown in section C-C of FIG. 14a Guide rod mating passage 247 provides rotational control and force to the guide rod 120 when it is inserted in the guide rod holder 240 and locked in the handle sub assembly 200. The shape of the guide rod mating passage 247 is illustrated as a hexagonal for convenience and can be any configuration complimentary to the guide rod 120.

Figure 15:
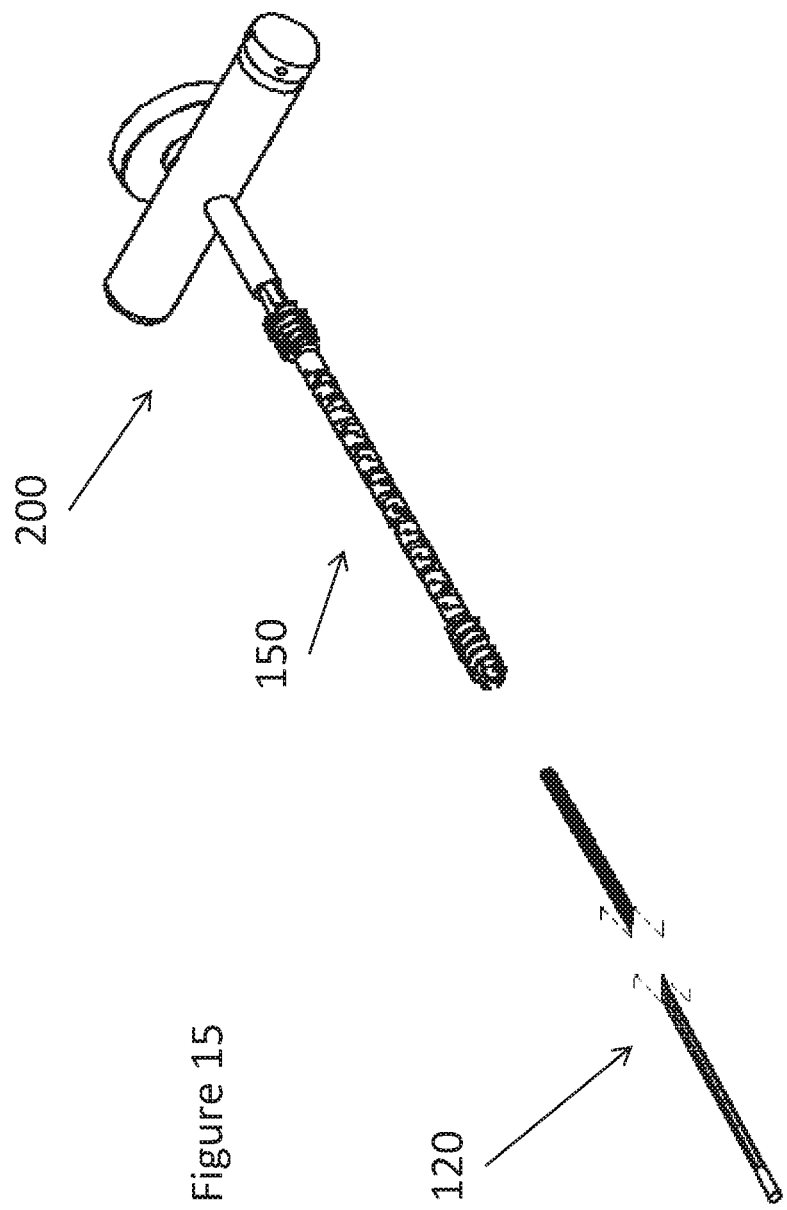
FIG. 15 shows the configuration of the handle sub-assembly 200 with attached fastening device 150 prior to inserting over the guide rod 120.

In FIG. 15, the fastening device 150 has been inserted on the handle sub-assembly 200 and is slid on the guide rod 120 (shown with in break way for clarity). The unique cross-sectional shape of the guide rod 120 conforms to the complimentary internal guide shape of the distal tapered surface 165 of fastening device. As well as the internal guide shape of the guide rod mating passage 247 of the guide rod holder 240.

Figure 16:
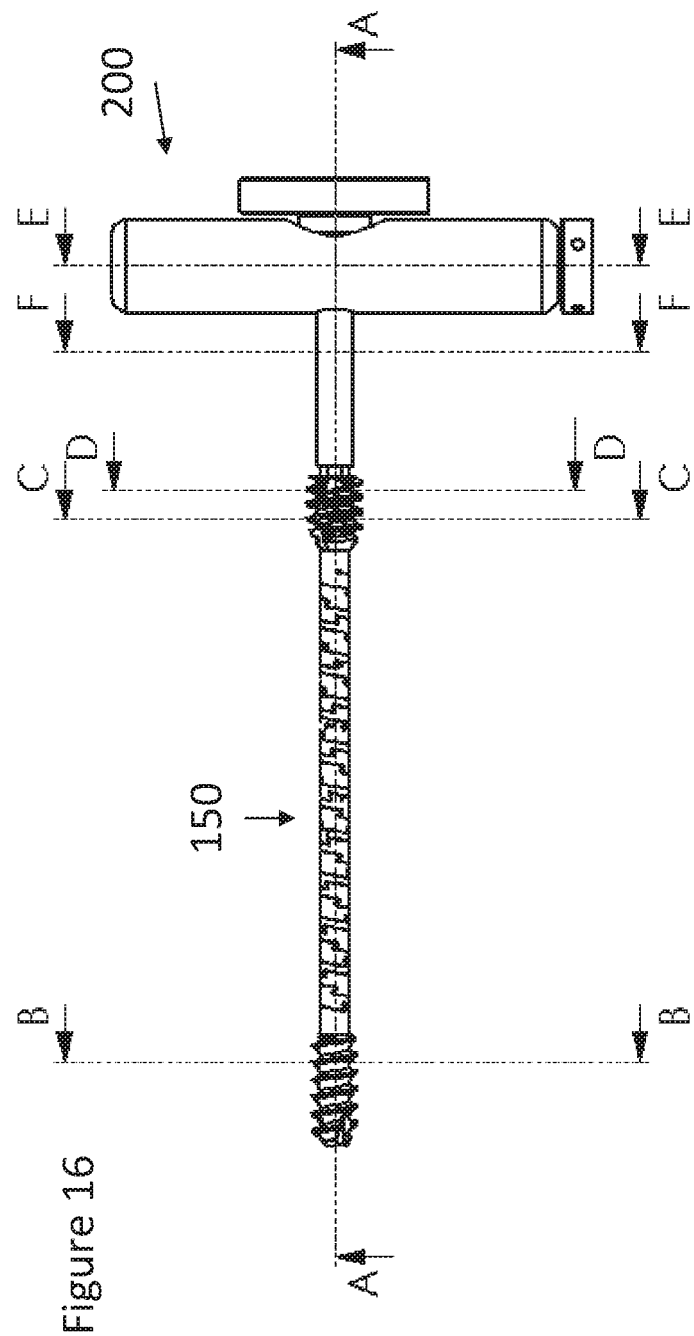
FIG. 16 shows a side view of the assembled tool assembly 100 and the locations for the sectional views in FIGS. 17A-G.

With the fastening device 150 fully inserted over the guide rod 120, the relationships of the parts can be examined in the sectional views presented in FIG. 16. During insertion the fastening device 150 is driven in contributing locations depicted at Section B-B, Section D-D, Section F-F and Section E-E Section A-A of FIG. 16 is shown in FIG. 17A showing the guide rod 120 fully through the length of the fastening device 150, passing through the fastener coupling mechanism 230 within the handle shank 220, and positioned within the guide rod holder 240. The guide rod 120 is maintained within the guide rod holder 240 by the guide rod holder clamp 250.

The cross-section B-B in FIG. 17B shows the complimentary relationship between the fastening device's threaded section 157 of the distal segment 156 and the distal tapered end section 125 of the guide rod 120. When the insertion torque is transmitted through the guide rod 120 to the distal tapered end 128, the guide rod rotates and interacts with the complimentary interior of the distal segment 156 of the fastening device 150 along the distal alignment surface 159. The distal gap 142 between the distal alignment surface 159 and the guide rod unthreaded surface 127 must sufficiently small to provide torque transmission but not to allow the guide rod 120 to rotate freely.

FIG. 17C shows the cross section at Section C-C in FIG. 17A with the guide rod threaded portion 122 within the distal section of the proximal segment 154, proximal mating surface 153, and the proximal receptacle 155.

FIG. 17D shows the cross section at Section D-D in FIG. 17A with the guide rod threaded portion 122 within the proximal section of the proximal segment 154. The fastening coupling mechanism 230 of the handle sub-assembly 200 is shown within the proximal segment 154 where the proximal mating surface 153 and proximal screw coupling 228 interact for insertion through the proximal gap 144. Also illustrated is the gap 146 between the handle shank 220 and the holder shaft 244.

FIG. 17E illustrates the Section E-E of the insertion tool handle 210 and the mechanism to lock the handle shank 220 within the guide rod holder clamp 250, When the guide rod holder clamp screw 255 is rotated into the guide rod holder clamp 250, the guide rod holder clamp screw 255 is drawn outward and the handle shank 220 is unable to rotate and held in place to transmit torque to the guide rod 120 captured within the guide rod holder clamp 250 and to the distal end of the fastening device 150.

FIG. 17F illustrates the cross-section F-F in FIG. 17A, through the handle shank 220 of the handle sub-assembly 200. The cross-section of the guide rod 120 is complimentary to the guide rod mating passage 247 (FIG. 14B) of the guide rod holder 240 to transmit the insertion or removal torque during installation once locked in place with the guide rod holder clamp 250. Prior to clamping, the holder shaft 244 of the guide rod holder 240 is free to rotate within the handle shank 220 to allow for the alignment of complimentary configurations between the guide rod 120 and the distal alignment surface 159 of the fastening device 150. Immediate locking of the holder shaft 244 within the handle shank 220 would make aligning the configurations difficult. Once aligned, the placement is locked into place through the tightening of the guide rod holder clamp screw 255, FIG. 17G provides a detailed view of the gap 146 and gap 148 between the guide rod 120 and the guide rod holder shaft 244. The circular configurations of the interior of the handle shank 220 and the exterior of the holder shaft 244 are dimensioned to form a gap 146 to permit rotation between the two parts. The hexagonal configuration between the guide rod 120 and the interior of the holder shaft 244 enables the gap 148 to prevent rotation between the two parts and allows the fastening device 150 to be rotated for manipulation. The size of the gaps 146 and 148 is dependent upon the size (diameter) of the fastening device 150 and the guide rod being used and will be known to those versed in the mechanical arts.

Figure 18:
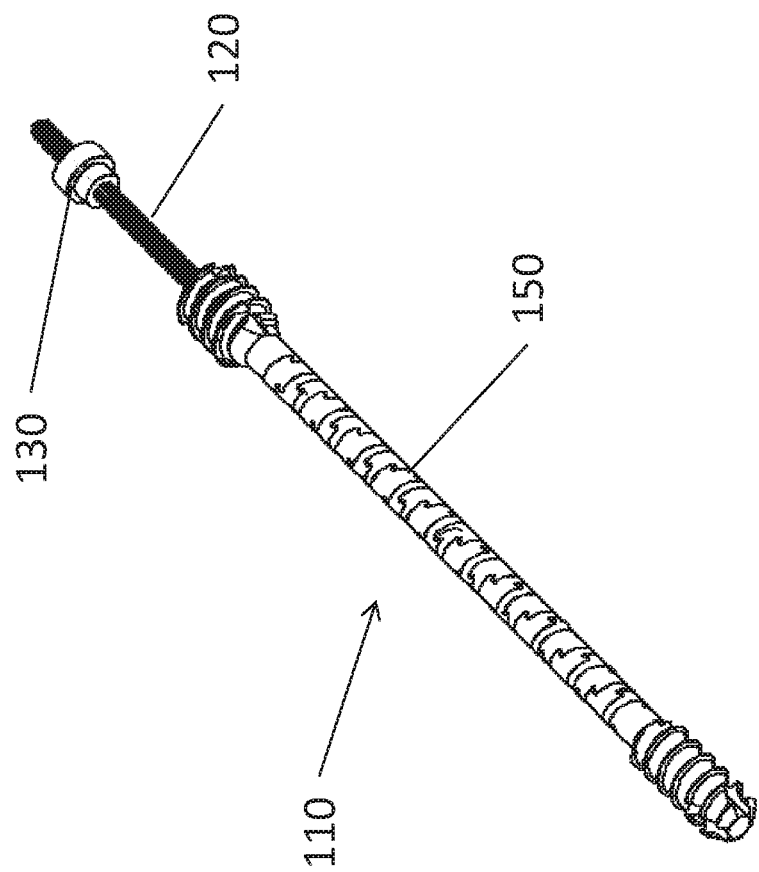
FIG. 18 shows the guide rod sub-assembly 110 with the associated locking nut 130 on the guide rod 120.
Figure 19:
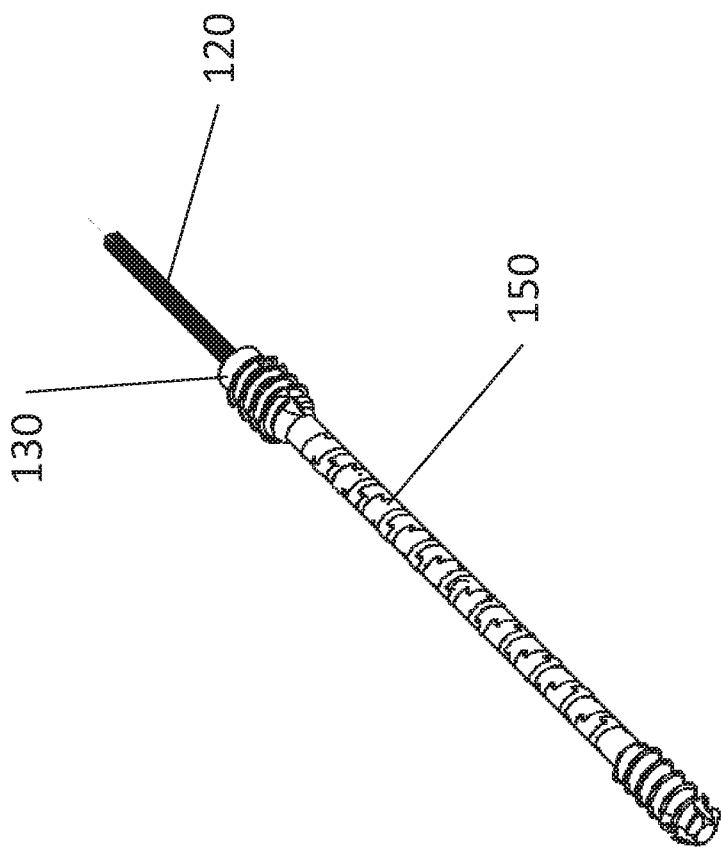
FIG. 19 show the guide rod sub-assembly 110 with the associated locking nut 130 fully on the guide rod 120.

With the fastening device 150 fully placed and engage, the handle sub-assembly 200 is disassembled and removed from attachment to the fastening device 150. The guide rod locking nut 130 is then threaded onto the threaded portion 122 of the guide rod 120, as illustrated in FIGS. 18 and 19.

The guide rod locking nut 130 can be tightened securely to the guide rod 120 with any tightening device known in the art appropriate for interaction with the locking nut 130.

The guide rod locking nut 130 is threaded down to the proximal end 164 of the fastening device 150. This draws the tapered end 128 of the guide rod 120 against the tapered distal end 162 of the fastening device 150 to compress and stiffen the fastening device 150. Once firmly in place the guide rod 120 is cut off proximal to the guide rod locking nut 130.

FIG. 20A shows the guide rod nut 130 fully engaged on the guide rod 120 and the location of Section A-A; As can be seen in FIGS. 20B and 20C, the head 132 of the locking nut 130 is in contact with the edge of the proximal segment 154 of the fastening device 150. The body 134 of the locking nut 130 extends into the proximal segment 154 to provide sufficient contact with the threads 124 of proximal threaded section 121 of the guide rod 120. The threads 136 of the locking nut 130 engage with the threads 124 of the guide rod 120, pulling the distal tapered end section 125 into the distal tapered internal surface 166 of the fastening device 150. Once tightened, the distal edge 126 of the distal tapered end section 125 is flush with the distal end 162 of the fastening device 150. As previously stated, the taper of the distal tapered end section 125 prevents the guide rod 120 from slipping. As the guide rod 120 pulls the distal end 162 of fastening device 150 toward the proximal section 121 of the guide rod 120, the helical slot is tightened, forcing the teeth to interlock in position.

In preparation for use the guide rod holder clamp 250 is placed in the clamp orifice 212 with the guide rod hole 254 positioned to receive the holder shaft 244 of the guide rod assembly 238. The holder shaft 244 is placed in the handle 210, through the guide rod hole 254 and into the holder shank 220. The proximal threaded section 121 of the guide rod 120 is slid first through the distal segment 156 of the fastening device 150 until the distal tapered end section 125 comes in contact with the distal end 162. The proximal threaded section 121 is then run though the guide rod channel 228 to engage with the guide rod mating surface 247. The complimentary configurations between the guide rod mating surface 247 and the distal alignment surface 159, once aligned, enable coordinated rotational movement between the guide rod 120 and the guide rod assembly 238. Once alignment is achieved, the guide rod holder clamp screw 255 is tightened with in guide rod holder clamp 250, applying pressure to the threaded section 121 and locking the guide rod 120 in position. Once the fastening device 150 is in position the handle sub-assembly 200 is removed and the locking nut 130 tightened as described heretofore. Any extra length of the guide rod 120 is then cut flush with the locking nut 130.

Figure 21:
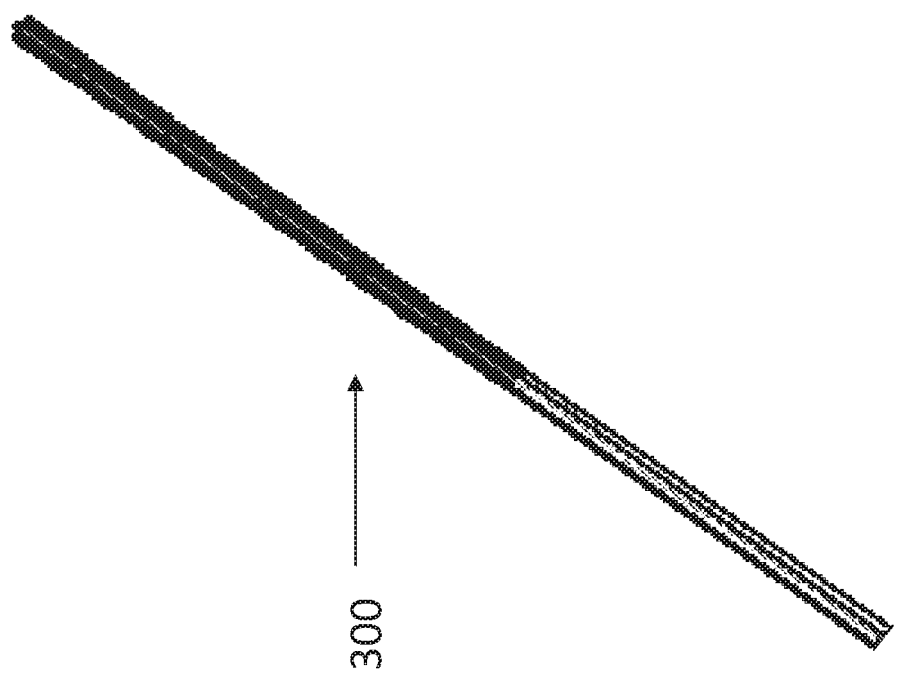
FIG. 21 is an alternate embodiment of a guide rod 300.

FIG. 21 illustrates an embodiment of the guide rod 300 for use with fastening devices without the tapered internal surface 166. As with the threaded portion 122 of the guide rod 120 the threaded section 302 of the guide rod 300 is locked into position for rotation by the guide rod holder clamp 250.

Figure 22:
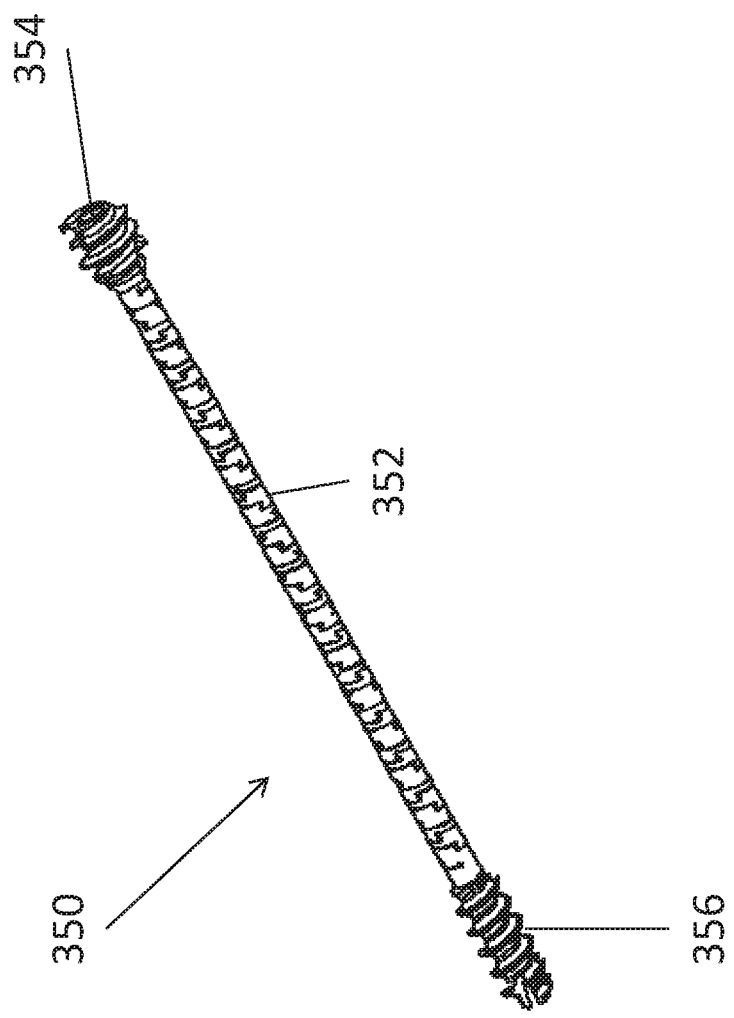
FIG. 22 is an alternate embodiment of a fastening device 350.

FIG. 22 shows a fastening device for medical use, in this example a bone screw 150 such as disclosed in U.S. Pat. No. 10,136,930 B2, into which the driver 200 inserted in order to insert or remove the screw 150. The screw 150 is composed of three sections; proximal segment 154 for driver attachment, a central flexible segment 152 and a distal segment 156 having distal screw threads 157.

The use of the embodiment illustrated in FIGS. 21 and 22 in conjunction with the tool assembly 100 and handle sub-assembly 200 are the same as the fastening device 150 with the exclusion of the distal tapered surface 165.

To use the disclosed handle sub-assembly 200 to remove a fastening device 150, the guide rod locking nut 130 is removed and the fastener coupling mechanism 230 reengaged with the proximal segment 154 of the fastening device 150. The rotation of the handle sub-assembly 200 is reversed and the fastening device is removed simultaneously from both the distal end 162 and the proximal end 164.

What is claimed is:

1. A tool assembly for manipulating a fastening device (150) of at least one element, said tool assembly comprising:
   a. a flexible guide rod (120), said flexible guide rod (120) comprising:
      i. a proximal threaded section (121), said proximal threaded section (121) having a proximal end;
      ii. a mid-section (123);
      iii. a distal section (125), said distal section (125) having a tapered distal end (128);
      iv. a length, said length extending from said proximal end of said proximal threaded section (121) to said tapered distal end (128) and having at least one cross-section configuration;
   b. a fastening device (150) having a distal segment (156) with an open tapered distal end (162); a proximal segment (154) with an open proximal end (164); a central flexible segment (152) extending from said distal segment (156) to said proximal segment (154); and a fastener channel (167) extending through said fastening device (150) from said tapered distal end (162) to a proximal receptacle (155) within said proximal end (164), wherein said fastener channel (167) has at least one cross-section configuration and is configured to receive said flexible guide rod (120); and
   c. a handle sub-assembly (200); said handle sub-assembly (200) comprising:
      i. a handle (210) having:
         1. a first end,
         2. a second end;
         3. a top side having a handle shank receiving area (211);
         4. a bottom side open to said handle shank receiving area (211);
         5. a clamp orifice (212) extending into said handle (210) from said first end past a mid-point of said handle (210);
      ii. a coupling mechanism (230) configured to receive said proximal receptacle (155);
      iii. a guide rod channel (228) extending through said coupling mechanism (230) configured to receive said proximal end of said flexible guide rod (120);
      iv. a handle shank (220), said handle shank (220) extending from said bottom side of said handle (210) to connect said handle (210) and a proximal end of said coupling mechanism (230);
      v. a guide rod shank passage (222) extending from said guide rod channel (228) and through said handle shank (220) and said handle (210);
      vi. a guide rod holder clamp (250) having a securing member receiving area and being dimensioned to be received within said clamp orifice (212);
      vii. a guide rod hole (254) dimensioned along said guide rod holder clamp (250) to align with said guide rod shank passage (222) and dimensioned to receive said flexible guide rod (120);
      viii. a guide rod holder clamp securing member (255); and
      ix. a guide rod holder assembly (238), said guide rod holder assembly (238) comprising:
         1. a guide rod holder (240); and
         2. a holder shaft (244), said holder shaft (244) having:
            a. a guide rod mating passage (247) extending through a distal portion of said holder shaft (244); and
            b. a guide rod shaft passage (245) extending through a proximal portion of said holder shaft (244) and said guide rod holder (240); said guide rod shaft passage (245) being dimensioned to receive said flexible drive rod (120);
   wherein one of said at least one cross-section configuration of said flexible guide rod is configured to interact with at least one of said at least one cross-section configuration of said fastening device channel (167) to enable said fastening device to be manipulated within said at least one element by initiating rotation of said fastening device at said tapered distal end.

2. The tool assembly of claim 1 wherein said distal section (125) of said flexible guide rod (120) is tapered, said distal section (125) having a proximal end and a distal end (128), said proximal end adjacent said mid-section (123) of said flexible guide rod (120).

3. The tool assembly of claim 2 wherein said distal end (128) of said distal section (125) has an outward taper.

4. The tool assembly of claim 3 wherein said outward taper is about 1 degree for a Morse taper fit.

5. The tool assembly of claim 3 wherein said outward taper is less than 90 degrees.

6. The tool assembly of claim 1 wherein said distal tapered section (125) is dimensioned to engage with a tapered internal surface (166) of said distal end (156) of said fastening device (150).

7. The tool assembly of claim 6 wherein said tapered internal surface (166) of said fastening device (150) is dimensioned to prevent said distal end (128) of said distal section (125) from passing through said distal end (162) of said fastening device (150).

8. The tool assembly of claim 1 wherein said guide rod mating passage (247) has a cross-section complimentary to said guide rod (120) to enable rotation of said guide rod (120) by said guide rod holder (240).

9. The tool assembly of claim 1 wherein said midsection (152) of said fastening device (150) is flexible to enable connection of more than one of said at least one element having non-linear connection channels.

10. The tool assembly of claim 1 wherein said fastening device (150) further comprises threads (157) along said distal segment (156), threads (158) along said proximal segment (154), and at least one sinuous slot (160) along said midsection (152) to allow flexibility of said fastening device.

11. The tool assembly of claim 1 wherein said flexible guide rod (120) is dimensioned to extend through said proximal receptacle (155) of said fastening device (150) and engage with said guide rod mating passage (247).

12. The tool assembly of claim 1 wherein said fastener coupling mechanism (230) has a cross section complementary to a cross section of a proximal mating surface (153) of said open proximal end (164) of said fastening device (150).

13. The tool assembly of claim 1 wherein said at least one cross-section of said fastening device channel (167) is a cross-section of a distal alignment surface (159) within said fastening device (150) and is complimentary to said predetermined configuration of said guide rod 120.

14. The tool assembly of claim 1 wherein said fastening device (150) is a bone screw.

15. The tool assembly of claim 1 wherein said guide rod (120) has a cross section less than an interior cross section of said distal segment (156) to create a gap (142) for torque transmission while enabling manipulation of said fastening device (150).

16. The tool assembly of claim 1 wherein said guide rod shaft passage (245) is circular.

17. The tool assembly of claim 1 wherein said securing member receiving area of said guide rod holder clamp (250) is interior threads (252) and said tightening member is a guide rod holder clamp screw (255) having clamp screw threads (257) to interact with said interior threads (252).

18. The tool assembly of claim 1 wherein material comprising said flexible guide rod is selected from the group consisting of Nitinol, spring steel, flexible polymers and flexible composites.

19. The tool assembly of claim 1 wherein said guide rod (120) has a cross section less than said holder shaft passage (245) of said guide rod shaft (244) to create a gap (148) for torque transmission while enabling manipulation of said fastening device (150).

20. The tool assembly of claim 1 further comprising a locking nut having interior threads (136) dimensioned to be received on said guide rod (120) proximal threaded section (121).

21. The tool assembly of claim 20 wherein said locking nut further comprises a body (130) dimensioned to be received within said proximal receptacle (155) of said fastening device (150).

22. A method of manipulating a fastening device using a tool assembly comprising the steps of:
  a. inserting a guide rod holder clamp (250) having a guide rod hole (254) and a threaded receiving area into a clamp orifice (212) within a handle (210) of a handle sub-assembly (200);
  b. Aligning said guide rod hole (254) with a holder shaft receiving area (211) within handle (210);
  c. extending a holder shaft (244) of a guide rod assembly (238) through said holder shaft receiving area (211) and into a handle shank (220) extending from a bottom side of said handle (210) to a coupling mechanism (230);
  d. inserting a proximal threaded section (121) of a flexible guide rod (120), having at least one cross-sectional configuration, into an open tapered distal end (162) of a fastening device (150) having a fastener channel (167) with a cross-sectional configuration;
  e. extending said flexible guide rod threaded section (121) through a distal segment (156) and a central flexible segment (152) to extend beyond a proximal segment (154) of said fastening device (150);
  f. continuing to insert said flexible guide rod (120) through said fastener channel (167) until a tapered distal end (128) of a distal section (125) of said guide rod (120) contacts said open tapered distal end (162) of said fastening device (150);
  g. inserting said threaded section (121) of said flexible guide rod (120) into a guide rod channel (228) within said coupling mechanism (230);
  h. inserting said coupling mechanism (230) into a proximal receptacle (155) within a proximal segment (154) of said fastening device (150);
  i. aligning a cross-section configuration of said proximal receptacle (155) with a cross section configuration of said coupling mechanism (230);
  j. aligning a cross section configuration of said threaded section (121) with a cross section configuration of said guide rod shaft passage (245) of holder shaft (244);
  k. preventing movement of said holder shaft (244) by pulling said guide rod hole (254) against said holder shaft (244) by inserting a threaded securing member into said guide rod holder clamp (250);
  l. manipulating said fastening device (150) by rotating said guide rod holder (240) within said guide rod assembly (238) to engage a tapered distal section (125) of guide rod (120) with fastener channel (167) at said distal segment (156) of said fastening device (150) to initiate rotation of said of said fastening device (150) at said tapered distal end (128);
  m. removing said handle sub-assembly (200) when said fastening device (150) is positioned;
  n. threading a nut (130) onto said threaded section (121);
  o. pulling said tapered distal section (125) into said tapered distal end (162) of said fastening device (150) by tightening said nut (130); and
  p. removing excess threaded section (121).

* * * * *